(12) United States Patent
Dow et al.

(10) Patent No.: US 7,247,628 B2
(45) Date of Patent: Jul. 24, 2007

(54) CANNABINOID RECEPTOR LIGANDS AND USES THEREOF

(75) Inventors: Robert L. Dow, Groton, CT (US); Marlys Hammond, Blue Bell, PA (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 337 days.

(21) Appl. No.: 10/702,149

(22) Filed: Nov. 4, 2003

(65) Prior Publication Data

US 2004/0122074 A1 Jun. 24, 2004

Related U.S. Application Data

(60) Provisional application No. 60/432,911, filed on Dec. 12, 2002.

(51) Int. Cl.
C07D 413/04 (2006.01)
C07D 231/12 (2006.01)
A61K 31/5377 (2006.01)
A61K 31/417 (2006.01)
A61K 31/415 (2006.01)

(52) U.S. Cl. .................. 514/236.5; 514/400; 514/406; 544/140; 548/333.5; 548/374.1; 548/375.1

(58) Field of Classification Search ................ 546/208; 548/374.1
See application file for complete search history.

(56) References Cited

U.S. PATENT DOCUMENTS

| | | | |
|---|---|---|---|
| 4,925,846 A | 5/1990 | Deacon et al. | |
| 4,944,790 A | 7/1990 | Moser et al. | |
| 5,134,142 A | 7/1992 | Matsuo et al. | |
| 5,462,960 A | 10/1995 | Barth et al. | |
| 5,470,862 A * | 11/1995 | Lin et al. .................... | 514/341 |
| 5,596,106 A | 1/1997 | Cullinan et al. | |
| 5,624,941 A | 4/1997 | Barth et al. .................. | 514/326 |
| 5,744,491 A | 4/1998 | Boigegrain et al. | |
| 5,744,493 A | 4/1998 | Boigegrain et al. | |
| 5,747,524 A | 5/1998 | Cullinan et al. | |
| 5,925,768 A | 7/1999 | Barth et al. | |
| 6,028,084 A | 2/2000 | Barth et al. | |
| 6,100,259 A | 8/2000 | Xiang et al. | |
| 6,344,474 B1 | 2/2002 | Maruani et al. | |
| 6,355,631 B1 | 3/2002 | Bouchard et al. | |
| 6,432,984 B1 | 8/2002 | Barth et al. | |
| 6,476,060 B2 | 11/2002 | Lange et al. | |
| 6,479,479 B2 | 11/2002 | Achard et al. | |
| 6,509,367 B1 | 1/2003 | Martin et al. | |
| 6,518,264 B2 | 2/2003 | Achard et al. | |
| 6,531,492 B1 | 3/2003 | Lundy et al. ................. | 514/341 |
| 6,566,356 B2 | 5/2003 | Achard et al. | |
| 2001/0027193 A1 | 10/2001 | Achard et al. | |
| 2001/0053788 A1 | 12/2001 | Lange et al. | |
| 2002/0019383 A1 | 2/2002 | Achard et al. | |
| 2002/0019421 A1 | 2/2002 | Biberman et al. | |
| 2002/0035102 A1 | 3/2002 | Achard et al. | |
| 2002/0091114 A1 | 7/2002 | Plot-Grosjean et al. | |
| 2002/0119972 A1 | 8/2002 | Leftheris et al. | |
| 2002/0128302 A1 | 9/2002 | Maruani et al. | |
| 2002/0188007 A1 | 12/2002 | Barth et al. | |
| 2003/0003145 A1 | 1/2003 | Abramovici et al. | |
| 2003/0055033 A1 | 3/2003 | Achard et al. | |
| 2003/0114495 A1 | 6/2003 | Finke et al. | |
| 2003/0139386 A1 | 7/2003 | Cote et al. | |
| 2003/0199536 A1 | 10/2003 | Thomas et al. | |
| 2004/0072833 A1 | 4/2004 | Nakai et al. | |
| 2004/0077650 A1 | 4/2004 | Dow | |
| 2004/0092520 A1 | 5/2004 | Griffith | |

FOREIGN PATENT DOCUMENTS

| | | |
|---|---|---|
| EP | 293220 B1 | 8/1994 |
| EP | 1354884 | 10/2003 |
| WO | WO 96/02248 A1 | 2/1996 |
| WO | WO 9614302 | 5/1996 |
| WO | WO 00/15609 A1 | 5/2000 |
| WO | WO 01/24798 A1 | 4/2001 |
| WO | WO 01/28557 A1 | 4/2001 |
| WO | WO 01/29007 A1 | 4/2001 |

(Continued)

OTHER PUBLICATIONS

Obach, Drugs of Today 39(5), p. 301-338 (2003).*
Muccioli et al., "Synthesis and Activity of 1,3,5-Triphenylimidazolidine-2,4-diones and 1,3,5-Triphenyl-2-thioxoimidazolidin-4-ones: Characterization of New CB1 Cannabinoid Receptor Inverse Agonists/Antagonists," J. Med. Chem., vol. 49, pp. 872-882 (2006).*
Lallemand et al., "SR147778, a CB1 Cannabinoid Receptor Antagonist, Suppresses Ethanol Preference in Chronically Alcoholized Wistar Rats," Alcohol, vol. 39, pp. 125-134 (2006).*
Ramirez et al., "Prevention of Alzheimer's Disease Pathology by Cannabinoids: Neuroprotection Mediated by Blockade of Microglial Activation," J. Neuroscience, 25(8), pp. 1904-1913 (2005).*

(Continued)

Primary Examiner—Kamal Saeed
Assistant Examiner—Andrew B. Freistein
(74) Attorney, Agent, or Firm—Julie M. Lappin

(57) ABSTRACT

Compounds of Formula (I) that act as cannabinoid receptor ligands and their uses in the treatment diseases, conditions and/or disorders herein.

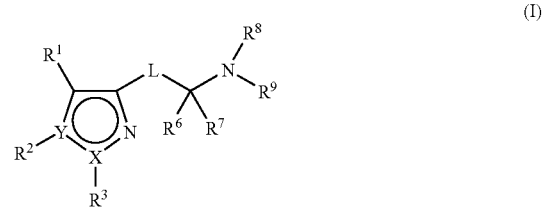

11 Claims, No Drawings

FOREIGN PATENT DOCUMENTS

| WO | WO 0129007 | 4/2001 |
|---|---|---|
| WO | WO 01/32629 A1 | 5/2001 |
| WO | WO 01/32663 A2 | 5/2001 |
| WO | WO 01/58450 A2 | 8/2001 |
| WO | WO 01/85092 A2 | 11/2001 |
| WO | WO 02 053565 | 7/2002 |
| WO | WO 02/076949 A1 | 10/2002 |
| WO | WO 03/006007 A1 | 1/2003 |
| WO | WO 03/007887 A2 | 1/2003 |
| WO | WO 03/018060 A1 | 3/2003 |
| WO | WO 03/020217 A2 | 3/2003 |
| WO | WO 03/020314 A1 | 3/2003 |
| WO | WO 03/026647 A1 | 4/2003 |
| WO | WO 03/026648 A1 | 4/2003 |
| WO | WO 03/027069 A1 | 4/2003 |
| WO | WO 03/027076 A2 | 4/2003 |
| WO | WO 03/027114 A1 | 4/2003 |
| WO | WO 03027076 | 4/2003 |
| WO | WO 03/040107 A1 | 5/2003 |
| WO | WO 03/051850 A1 | 6/2003 |
| WO | WO 03/051851 A1 | 6/2003 |
| WO | WO 03/075660 A1 | 9/2003 |
| WO | WO 03/077847 A2 | 9/2003 |
| WO | WO 03/078413 A1 | 9/2003 |
| WO | WO 03/082190 A2 | 10/2003 |
| WO | WO 03/082191 A2 | 10/2003 |
| WO | WO 03/082256 A2 | 10/2003 |
| WO | WO 03/082833 A1 | 10/2003 |
| WO | WO 03/084943 A2 | 10/2003 |
| WO | WO 03/086288 A2 | 10/2003 |
| WO | WO 03/087037 A1 | 10/2003 |
| WO | WO 03 095455 | 11/2003 |
| WO | WO 2004/012617 A2 | 2/2004 |

OTHER PUBLICATIONS

Roger G. Pertwee, Current Medicinal Chemistry, 1999, vol. 6, pp. 635-664, "Pharmacology of Cannabinoid Receptor Ligands".

Brian F. Thomas et al., The Journal of Pharmacology and Experimental Therapies, 1998, vol. 285, No. 1, pp. 285-292, "Comparative Receptor Binding Analyses of Cannabinoid Agonists and Antagonists".

Tzavara, E.T., et al., "The CB1 Receptor Antagonist SR141716A selectively increases monoaminergic neurotransmission in the medial prefrontal cortex: Implications for Therapeutic Actions," *J Pharmacol*, 138, 544-553 (2003).

Racz, I., et al., "A Critical Role for the Cannabinoid CB1 Receptors in Alcohol Dependence and Stress-Stimulated Ethanol Drinking," *J Neurosci*, 23(6), 2453-2458 (2003).

Croci, T., et al., "Role of Cannabinoid CB1 Receptors and Tumor Necrosis Factor-$\alpha$ in the gut and systemic anti-inflammatory activity of SR 141716 (Rimonabant) in rodents," *Brit J Pharmacol*, 140, 115-122 (2003).

DaSilva, G.E., et al., "Potentiation of Penile Erection and Yawning Responses to Apomorphine by Cannabinoid Receptor Antagonists in Rats," *Neurosci Let*, 349, 49-52 (2003).

Wang, L., et al., "Endocannabinoid Signaling via Cannabinoid Receptor 1 is involved in Ethanol Preference and its Age-Dependent Decline in Mice," *PNAS*, 100(3), 1393-1398 (2003).

Ruiu, S., et al., "Synthesis and Characterization of NESS 0327: A Novel Putative Antagonist of the CB1 Cannabinoid Receptor," *J Pharmacol Exp Therap*, 306, 363-370 (2003).

Howlett, A.C., et al., "International Union of Pharmacology. XXVII. Classification of Cannabinoid Receptors," *Pharmacol Rev*, 54, 161-202 (2002).

Gomez, R., et al., "A Peripheral Mechanism for CB1 Cannabinoid Receptor-Dependent Modulation of Feeding," *J. Neurosci*, 22(21), 9612-9617 (2002).

Wiley, J.L., et al., "Novel Pyrazole Cannabinoids: Insights into CB1 Receptor Recognition and Activation," *J Pharmacol Exp Therap*, 296(3), 1013-1022 (2001).

Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).

Pertwee, R.G., "Cannabinoids and the Gastronintestinal Tract," *Gut*, 48, 859-867 (2001).

Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).

Hungund, B.L. and B.S. Basavarajappa, "Are Anadamide and Cannabinoid Receptors involved in Ethanol Tolerance? A Review of the Evidence," *Alcohol & Alcoholism*. 35(2) 126-133, (2000).

Freedland, C.S., et al., "Effects of SR141716A, a Central Cannabinoid Receptor Antagonist, on Food-maintained Responding," *Pharmacol Biochem Behav*, 67, 265-270 (2000).

Lan, R., et al., "Structure-Activity Relationships of Pyrazole Derivatives as Cannabinoid Receptor Antagonists" *J. Med. Che.m*, 42, 769-776 (1999).

Pertwee, R.G., "Pharmacology of Cannabinoid Receptor Ligands" *Curr Med Chem*, 6, 635-664 (1999).

Basavarajappa, B.S., et al., "Chronic Ethanol Administration Downregulates Cannabinoid Receptors in Mouse Brain Synaptic Plasma Membrane," *Brain Res*, 793, 212-218 (1998).

Thomas, B.F., et al., "Comparative Receptor Binding Analyses of Cannabinoid Agonists and Antagonists," *J Pharmacol Exp Therap*, 285, 285-292 (1998).

Colombo, G., et al., "Appetite Suppression and Weight Loss after the Cannabinoid Antagonist SR141716," *Life Sci.*, 63, PL113-PL117 (1998).

Simiand, J., et al., "SR141716, a CB1 Cannabinoid Receptor Antagonist, Selectively Reduces Sweet Food Intake in Marmose," *Behav. Pharmacol.*, 9, 179-181 (1998).

Chaperon, F., et al., "Involvement of Central Cannabinoid (CB1) Receptors in the Establishment of Place Conditioning in Rats," *Psychopharmacology*, 135, 324-332 (1998).

Arnone, M., et al., "Selective Inhibition of Sucrose and Ethanol Intake by SR141716, an Antagonist of Central Cannabinoid (CB1) Receptors," *Psychopharmacol*, 132, 104-106 (1997).

Savontaus, E., et al., "Anti-Obesity Effect of MPV-1743 A III, a Novel Imidazoline Derivative, in Genetic Obesity," *Eur J Pharmacol*, 328, 207-215 (1997).

Sanudo-Pena, M.C., et al., "Endogenous Cannabinoids as an Aversive or Counter-rewarding System in the Rat," *Neurosci Let*, 223, 125-128 (1997).

Gifford, A.N., et al., "Electrically Evoked Acetylcholine Relase from Hippocampal Silices is Inhibited by the Cannabinoid Receptor Agonist, WIN 55212-2 and is Potentiated by the Cannabinoid Antagonist, SR 141716A," *J Pharmacol Exp Ther*, 277, 1431-1436 (1996).

Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).

Mansbach, R.S., et al., "Effects of Cannabinoid CB1 Receptor Antagonist SR141716A on the Behavior of Pigeons and Rats," *Psychopharmacology*, 124, 315-322 (1996).

Lichtman, A.H., et al., "Delta-9-Tetrahydrocannabinol Impairs Spatial Memory through a Cannabinoid Receptor Mechanism," *Psychopharmacology*, 126, 125-131 (1996).

Perio, A., et al., "Central Mediation of the Cannabinoid Cue: Activity of a Selective CB1 Antagonist, SR141716A," *Behavioral Pharmacology*, 7, 65-71 (1996).

Rinaldi-Carmona, M., et al., "Biochemical and Pharmacological Characteriszation of SR141716A, The First Potent and Selective Brain Cannabinoid Receptor Antagonist," *Life Sci*, 56, 1941-1947 (1995).

Pertwee, R., et al., "AM630, A Competitive Cannabinoid Receptor Antagonist," *Life Sci*, 56, 1949-1955 (1995).

Rinaldi-Carmona, M., et al., "SR141716A, a Patent and Selective Antagonist of the Brain Cannabinoid Receptor," *FEBS Letters*, 350, 240-244 (1994).

Dutta, A., et al., "The Synthesis and Pharmacological Evaluation of the Cannabinoid Antagonist SR 141716A", *Med. Chem. Rev.* 5, 54-62 (1994).

Drummond, J., et al., "Evaluation and Synthesis of Aminohydroxyisoxazoles and Pyrazoles as Potential Glycine Agonists," *J. Med. Chem*, 32, 2116-2128 (1989).

Murray, W., et al., "A Simple Regioselective Synthesis of Ethyl 1,5-Diarylpyrazole-3-carboxylates" *J. Heterocyclic Chem*, 26, 1389 (1989).

Dewey, W.L., "Cannabinoid Pharmacology," *Pharmacological Reviews*, 38(2)m 151-178 (1986).

Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 39(1) 129-136 (1983).

Birkofer, L. and K. Richtzenhain, "Silyl-Derivate von Pyrazol, Isoxazol und 1,2,3-Triazol" *Chem. Ber.* 112, 2829-2836 (1979).

Franke, H. et al., "Polare Cycloadditionen von elektronenreichen Mehrfach-bindungssystemen an 1,3,4-oxadiazolium-Salze: Synthase von 3aH-[1,3,4]Oxadiazolo[3,2-a]chinolinen" *Chem. Ber.* 112, 3623-3636 (1979).

Sucrow, W., et al., "Bimolekulare Cyclisierung von 2-(1-Methylhydrazino)maleinsaure-dimethylester" *Chem. Ber.* 112, 1712-1718 (1979).

\* cited by examiner

CANNABINOID RECEPTOR LIGANDS AND USES THEREOF

This application claims the benefit of U.S. Provisional Application No. 60/432,911 filed on Dec. 12, 2002 and incorporated herein by reference in its entirety.

FIELD OF THE INVENTION

The present invention relates to pyrazole and imidazole compounds, which are useful as cannabinoid receptor ligands, in particular as CB-1 receptor antagonists. As a result, the present invention also relates to the use of the compounds in treating diseases, conditions and disorders modulated by cannabinoid receptor ligands including pharmaceutical compositions for such use.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25–29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207–12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5–10% loss of body weight can substantially improve metabolic values, such as blood glucose, blood pressure, and lipid concentrations. Hence, it is believed that a 5–10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.*, 3(suppl 4), 415s–7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol*, 132, 104–106 (1997); Colombo, G., et al., "Appetite Suppression and Weight Loss after the Cannabinoid Antagonist SR141716," *Life Sci.*, 63, PL113–PL117 (1998); Simiand, J., et al., "SR141716, a CB1 Cannabinoid Receptor Antagonist, Selectively Reduces Sweet Food Intake in Marmose," *Behav. Pharmacol.*, 9, 179–181 (1998); and Chaperon, F., et al., "Involvement of Central Cannabinoid (CB1) Receptors in the Establishment of Place Conditioning in Rats," *Psychopharmacology*, 135, 324–332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs*, 9(7), 1553–1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol*, 132, 104–106 (1997). For a review, see Hungund, B. L and B. S. Basavarajappa, "Are Anadamide and Cannabinoid Receptors involved in Ethanol Tolerance? A Review of the Evidence," *Alcohol & Alcoholism.* 35(2) 126–133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) that act as cannabinoid receptor ligands (preferably, CB1 receptor antagonists or inverse agonists).

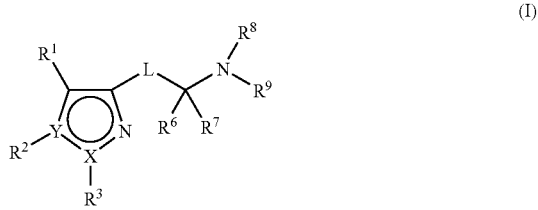

(I)

wherein

X is carbon and Y is nitrogen or X is nitrogen and Y is carbon;

R¹ is hydrogen, (C₁–C₆)alkyl, halogen, or cyano;

R² and R³ are each independently (CH₂)ₙ-aryl or (CH₂)ₙ-heteroaryl, where n is 0, 1 or 2, and where the aryl and the heteroaryl moieties are optionally substituted with one or more substituents (see list of substituents in the definition section below);

L is —C(O)— or —C(R⁴)(OR⁵)—, where R⁴ is hydrogen or (C₁–C₆)alkyl and R⁵ is hydrogen, (C₁–C₆)alkyl, or taken together with R⁸ or R⁹ is —CH₂CH₂— or —CH₂C(O)—;

R⁶ and R⁷ are each independently hydrogen or (C₁–C₆)alkyl, or R⁶ and R⁷ taken together form a partially or fully saturated carbocyclic ring; and R⁸ and R⁹ are each independently hydrogen, (C₁–C₆)alkyl, —C(O)(CH₂)ₘR¹⁰, —SO₂(CH₂)ₙR¹⁰, or —(CH₂)ₚR¹⁰, where m and n are 0, 1, or 2, p is 0, 1, 2 or 3, and R¹⁰ is selected from the group consisting of (C₁–C₈)alkyl, a partially or fully saturated cycloalkyl, aryl, heteroaryl, and a partially or fully saturated heterocycle, where the (C₁–C₈)alkyl, the cycloalkyl, the aryl, the heteroaryl and the heterocycle are optionally substituted with one or more substituents (see list of substituents in the definition section below); or R⁸ and R⁹ taken together form a partially or fully saturated, 4- to 8-membered heterocyclic ring containing 1 to 3 heteroatoms and optionally substituted with one or more substituents (see list of substituents in the definition section below); modulated by cannabinoid receptor antagonists in animals are described modulated by cannabinoid receptor antagonists in animals are described a pharmaceutically acceptable salt thereof, a prodrug of the compound or the salt, or a solvate or hydrate of the compound, the salt or the prodrug.

In a preferred embodiment, a compound of Formula (IA) is provided.

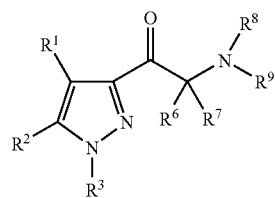

(IA)

wherein

R¹ is hydrogen or (C₁–C₆)alkyl;

R² and R³ are each independently —(CH₂)ₙ-aryl or —(CH₂)ₙ-heteroaryl, where n is 0, 1 or 2, and where the aryl and the heteroaryl moieties are optionally substituted with one to three substituents (preferably, n is 0, R² is p-chlorophenyl or p-fluorophenyl, and R³ is 2,4-dichlorophenyl, 2-chlorophenyl or 2-flurorophenyl);

R⁶ and R⁷ are each independently hydrogen or (C₁–C₆)alkyl, or R⁶ and R⁷ taken together form a partially or fully saturated carbocyclic ring; and R⁸ and R⁹ taken together form a partially or fully saturated, 5- to 7-membered heterocyclic ring containing 1 to 3 heteroatoms and optionally substituted with one or more substituents (see list of substituents in the definition section below);

a pharmaceutically acceptable salt thereof, a prodrug of the compound or the salt, or a solvate or hydrate of the compound, the salt or the prodrug.

Preferred compounds of Formula IA include: 1-[5-(4-chloro-phenyl)-1-(2-chloro-phenyl)-4-methyl-1H-pyrazol-3-yl]-2-piperidin-1-yl-ethanone; 1-[5-(4-chloro-phenyl)-1-(2-chloro-phenyl)-4-methyl-1H-pyrazol-3-yl]-2-morpholin-4-yl-ethanone; 1-[5-(4-chloro-phenyl)-1-(2-chloro-phenyl)-4-methyl-1H-pyrazol-3-yl]-2-[4-(1-methyl-1H-pyrrole-2-carbonyl)-piperazin-1-yl]-ethanone; 1-[5-(4-chloro-phenyl)-1-(2-chloro-phenyl)-4-methyl-1H-pyrazol-3-yl]-2-[4-(1-methyl-cyclopropanecarbonyl)-piperazin-1-yl]-ethanone; N-(1-{2-[5-(4-chloro-phenyl)-1-(2-chloro-phenyl)-4-methyl-1H-pyrazol-3-yl]-2-oxo-ethyl}-piperidin-4-yl)-2,2,2-trifluoro-acetamide; 1-[5-(4-chloro-phenyl)-1-(2-fluoro-phenyl)-4-methyl-1H-pyrazol-3-yl]-2-morpholin-4-yl-ethanone; 1-[5-(4-chloro-phenyl)-1-(2-fluoro-phenyl)-4-methyl-1H-pyrazol-3-yl]-2-piperidin-1-yl-ethanone; 1-[5-(4-chloro-phenyl)-1-(2-fluoro-phenyl)-4-methyl-1H-pyrazol-3-yl]-2-(4-trifluoroacetyl-piperazin-1-yl)-ethanone; 1-[1-(2-chloro-phenyl)-5-(4-chloro-phenyl)-4-methyl-1H-pyrazol-3-yl]-2-pyrrolidin-1-yl-ethanone; 1-[1-(2-chloro-phenyl)-5-(4-chloro-phenyl)-4-methyl-1H-pyrazol-3-yl]-2-[1,4]oxazepan-4-yl-ethanone; and 1-[5-(4-chloro-phenyl)-1-(2-chloro-phenyl)-4-methyl-1H-pyrazol-3-yl]-2-(1-oxa-8-aza-spiro[4.5]dec-8-yl)-ethanone; a pharmaceutically acceptable salt thereof, a prodrug of the compound or the salt, or a solvate or hydrate of the compound, the salt or the prodrug In another preferred embodiment of the present invention, compounds of Formula (IB) are provided.

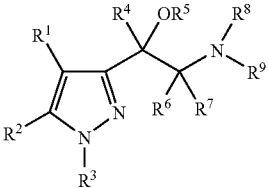

(IB)

wherein

R¹ is hydrogen or (C₁–C₆)alkyl;

R² and R³ are each independently —(CH₂)ₙ-aryl or —(CH₂)ₙ-heteroaryl, where n is 0, 1 or 2, and where the aryl and the heteroaryl moieties are optionally substituted with one to three substituents (preferably, n is 0, R² is p-chlorophenyl or p-fluorophenyl, and R³ is 2,4-dichlorophenyl, 2-chlorophenyl or 2-flurorophenyl);

R⁴ is hydrogen or (C₁–C₆)alkyl;

R⁵ is hydrogen or (C₁–C₆)alkyl;

R⁶ and R⁷ are each independently hydrogen or (C₁–C₆)alkyl, or R⁶ and R⁷ taken together form a partially or fully saturated carbocyclic ring; and R⁸ and R⁹ are each independently hydrogen, (C₁–C₆)alkyl, —C(O)(CH₂)ₘR¹⁰, —SO₂(CH₂)ₙR¹⁰, or —(CH₂)ₚR¹⁰, where m and n are 0, 1, or 2, p is 0, 1, 2 or 3, and R¹⁰ is selected from the group consisting of a (C₁–C₈)alkyl, a partially or fully saturated cycloalkyl, aryl, heteroaryl, and a partially or fully saturated heterocycle, where the (C₁–C₈)alkyl, the cycloalkyl, the aryl, the heteroaryl and the heterocycle are optionally substituted with one or more substituents (see list of substituents in the definition section below), or R⁸ and R⁹ taken together form a partially or fully saturated, 5- to 7-membered heterocyclic ring containing 1 to 3 heteroatoms and optionally substituted with one or more substituents (see list of substituents in the definition section below);

a pharmaceutically acceptable salt thereof, a prodrug of the compound or the salt, or a solvate or hydrate of the compound, the salt or the prodrug.

Preferred compounds of Formula IB include: 2-(benzyl-isopropyl-amino)-1-[1-(2-chloro-phenyl)-5-(4-chloro-phenyl)-4-methyl-1H-pyrazol-3-yl]-ethanol; 1-[5-(4-chloro-phenyl)-1-(2-chloro-phenyl )-4-methyl-1H-pyrazol-3-yl]-2-(3,5-dimethyl-piperidin-1-yl)-ethanol; 1-{2-[1-(2-chloro-phenyl)-5-(4-chloro-phenyl)-4-methyl-1H-pyrazol-3-yl]-2-hydroxy-ethyl}-4-isopropylamino-piperidine-4-carboxylic acid amide; 1-[5-(4-chloro-phenyl)-1-(2-chloro-phenyl)-4-methyl-1H-pyrazol-3-yl]-2-(3,3-dimethyl-piperidin-1-yl)-ethanol; 1-[5-(4-chloro-phenyl)-1-(2-chloro-phenyl)-4-methyl-1H-pyrazol-3-yl]-2-piperidin-1-yl-ethanol; and 1-[5-(4-chloro-phenyl)-1-(2-chloro-phenyl)-4-methyl-1H-pyrazol-3-yl]-2-morpholin-4-yl-ethanol; a pharmaceutically acceptable salt thereof, a prodrug of the compound or the salt, or a solvate or hydrate of the compound, the salt or the prodrug.

In yet another preferred embodiment of the present invention, compounds of Formula (IC) are provided.

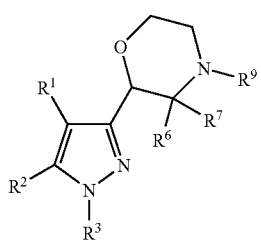

(IC)

wherein

R$^1$ is hydrogen or (C$_1$–C$_6$)alkyl;

R$^2$ and R$^3$ are each independently —(CH$_2$)$_n$-aryl or —(CH$_2$)$_n$-heteroaryl, where n is 0, 1 or 2, and where the aryl and the heteroaryl moieties are optionally substituted with one to three substituents (preferably, n is 0, R$^2$ is p-chlorophenyl or p-fluorophenyl, and R$^3$ is 2,4-dichlorophenyl, 2-chlorophenyl or 2-fluorophenyl);

R$^6$ and R$^7$ are each independently hydrogen or (C$_1$–C$_6$) alkyl, or R$^6$ and R$^7$ taken together form a partially or fully saturated carbocyclic ring; and R$^9$ is hydrogen, (C$_1$–C$_6$)alkyl, —C(O)(CH$_2$)$_m$R$^{10}$, —SO$_2$(CH$_2$)$_n$R$^{10}$, or —(CH$_2$)$_p$R$^{10}$, where m and n are 0, 1, or 2, p is 0, 1, 2 or 3, and R$^{10}$ is selected from the group consisting of (C$_1$–C$_8$)alkyl, a partially or fully saturated cycloalkyl, aryl, heteroaryl, and a partially or fully saturated heterocycle, where the (C$_1$–C$_8$)alkyl, the cycloalkyl, the aryl, the heteroaryl and the heterocycle are optionally substituted with one or more substituents (see list of substituents in the definition section below);

a pharmaceutically acceptable salt thereof, a prodrug of the compound or the salt, or a solvate or hydrate of the compound, the salt or the prodrug.

Preferred compounds of Formula (IC) include: 2-[5-(4-chloro-phenyl)-1-(2-chloro-phenyl)-4-methyl-1H-pyrazol-3-yl]-4-cyclohexyl-morpholine; 2-[5-(4-chloro-phenyl)-1-(2-chloro-phenyl)-4-methyl-1H-pyrazol-3-yl]-4-(propane-2-sulfonyl)-morpholine; 2-[5-(4-chloro-phenyl)-1-(2-chloro-phenyl)-4-methyl-1H-pyrazol-3-yl]-4-(toluene-4-sulfonyl)-morpholine; 1-{2-[1-(2-chloro-phenyl)-5-(4-chloro-phenyl)-4-methyl-1H-pyrazol-3-yl]-morpholin-4-yl}-2-methyl-propan-1-one; and 2-[1-(2-chloro-phenyl)-5-(4-chloro-phenyl)-4-methyl-1H-pyrazol-3-yl]-4-(4-trifluoromethyl-benzyl)-morpholine; a pharmaceutically acceptable salt thereof or a solvate or hydrate of the compound or the salt.

In yet another embodiment of the present invention, a compound of Formula (ID) is provided.

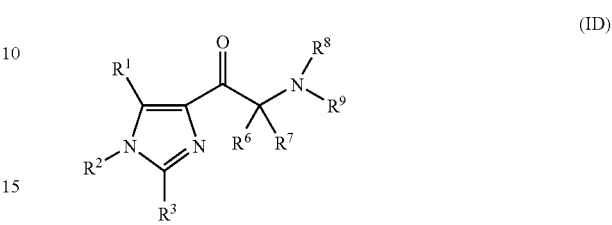

(ID)

wherein

R$^1$ is hydrogen or (C$_1$–C$_6$)alkyl;

R$^2$ and R$^3$ are each independently —(CH$_2$)$_n$-aryl or —(CH$_2$)$_n$-heteroaryl, where n is 0, 1 or 2, and where the aryl and the heteroaryl moieties are optionally substituted with one to three substituents (preferably, n is 0, R$^2$ is p-chlorophenyl or p-fluorophenyl, and R$^3$ is 2,4-dichlorophenyl, 2-chlorophenyl or 2-fluorophenyl);

R$^6$ and R$^7$ are each independently hydrogen or (C$_1$–C$_6$) alkyl, or R$^6$ and R$^7$ taken together form a partially or fully saturated carbocyclic ring; and R$^8$ and R$^9$ taken together form a partially or fully saturated, 5- to 7-membered heterocyclic ring containing 1 to 3 heteroatoms and optionally substituted with one or more substituents (see list of substituents in the definition section below);

a pharmaceutically acceptable salt thereof, a prodrug of the compound or the salt, or a solvate or hydrate of the compound, the salt or the prodrug.

Preferred compounds of formula (ID) include: 1-[1-(4-chloro-phenyl)-2-(2,4-dichloro-phenyl)-5-methyl-1H-imidazol-4-yl]-2-piperidin-1-yl-ethanone and 1-[1-(4-chloro-phenyl)-2-(2,4-dichloro-phenyl)-5-methyl-1H-imidazol-4-yl]-2-morpholin-4-yl-ethanone; a pharmaceutically acceptable salt thereof, a or a solvate or hydrate of the compound, or the salt.

Some of the compounds described herein contain at least one chiral center; consequently, those skilled in the art will appreciate that all stereoisomers (e.g., enantiomers and diastereoisomers) of the compounds illustrated and discussed herein are within the scope of the present invention. In addition, tautomeric forms of the compounds are also within the scope of the present invention.

In another aspect of the present invention, a pharmaceutical composition is provided that comprises (1) a compound of the present invention, and (2) a pharmaceutically acceptable excipient, diluent, or carrier.

In yet another embodiment of the present invention, a method for treating a disease, condition or disorder modulated by a cannabinoid receptor (preferably, a CB1 receptor) antagonists in animals that includes the step of administering to an animal in need of such treatment a therapeutically effective amount of a compound of the present invention (or a pharmaceutical composition thereof). Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, a typical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR4 agonists, CCK-A agonists, monoamine reuptake inhibitors, sympathomimetic agents, $β_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists, thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described above and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described above and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions and/or disorders modulated by cannabinoid receptor antagonists in an animal. The kit comprises a) a suitable dosage form comprising a compound of the present invention; and b) instructions describing a method of using the dosage form to treat diseases linked to the modulation of the cannabinoid receptor (preferably, the CB1 receptor).

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described above, and (ii) a pharmaceutically acceptable carrier, excipient or diluent; and c) a container.

Definitions

As used herein, the term "alkyl" refers to a hydrocarbon radical of the general formula $C_nH_{2n+1}$. The alkane radical may be straight or branched. For example, the term "$(C_1–C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). The alkane radical may be unsubstituted or substituted with one or more substituents (generally, one to three substituents except in the case of halogen substituents such as perchloro or perfluoroalkyls) selected from the group of substituents listed below in the definition for "substituted." For example, "halo-substituted alkyl" refers to an alkyl group substituted with one or more halogen atoms (e.g., fluoromethyl, difluoromethyl, trifluoromethyl, perfluoroethyl, and the like). Similarly, the alkyl portion of an alkoxy, alkylamino, dialkylamino, and alkylthio group has the same definition as above.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiro-fused ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. Generally, the carbocyclic ring is a 3 to 8 membered ring. In addition, the partially saturated or fully saturated cycloalkyl may be optionally substituted with one of more substituents (typically, one to three substituents) selected from the group of substituents listed below in the definition for "substituted." A substituted carbocyclic or heterocyclic ring includes groups wherein the carbocyclic ring is fused to a phenyl ring (e.g., indanyl, etc.) or a heteroaryl ring. The carbocyclic group may be attached to the chemical entity or moiety by any one of the carbon atoms within the carbocyclic ring system.

The term "partially saturated or fully saturated heterocyclic ring" (also referred to as "heterocycle") refers to nonaromatic rings that are either partially or fully hydrogenated and may exist as a single ring, bicyclic ring or a spiro-fused ring. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. Generally, the heterocycle is 3 to 8 membered ring containing 1 to 3 heteroatoms selected from oxygen, sulfur and nitrogen. In addition, the partially saturated or fully saturated heterocyclic groups may be optionally substituted with one of more substituents (typically, one to three substituents) selected from the group of substituents listed below in the definition for "substituted." A substituted heterocyclic ring includes groups wherein the heterocyclic ring is fused to a phenyl ring (e.g., 2,3-dihydrobenzofuranyl, 2,3-dihydroindolyl, 2,3-dihydrobenzothiophenyl, 2,3-dihydrobenzothiazolyl, etc.) or a heteroaryl ring. The heterocyclic group may be attached to the chemical entity or moiety by any one of the atoms within the heterocyclic ring system.

The term "alkenyl" refers to a hydrocarbon containing at least one carbon-carbon double bond. As described above for alkyl, the alkene radical may be straight or branched and the alkene radical may be unsubstituted or substituted with one or more substituents (typically, one to three substituents except for perhalo substitutions) selected from the group of substituents listed below in the definition for "substituted." The term "alkene" also includes all diastereoisomers (e.g., cis and trans isomers).

The term "aryl" or "aromatic carbocyclic ring" refers to aromatic moieties having single (e.g., phenyl) or fused ring system (e.g., naphthalene, anthracene, phenanthrene, etc.). Unless indicated otherwise, the aryl groups may be unsubstituted or substituted with one or more substituents (preferably no more than three substituents) selected from the group of substituents listed below in the definition for "substituted." Substituted aryl groups include a chain of aromatic moieties (e.g., biphenyl, terphenyl, phenylnaphthalyl, etc.) The aryl group may be attached to the chemical entity or moiety by any one of the carbon atoms within the aromatic ring system. Preferred aryl substituents are halogens (F, Cl, Br or I, preferably F or Cl), ($C_1$–$C_4$)alkoxy, ($C_1$–$C_4$)alkyl, halo-substituted($C_1$–$C_4$)alkyl (e.g., $CH_2F$, $CHF_2$ and $CF_3$) and cyano. Similarly, the aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteroatom (e.g., oxygen, sulfur, nitrogen or combinations thereof) within the aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms selected from oxygen, sulfur and nitrogen and a typical fused heteroaryl ring system is a 9- to 10-membered ring system containing one to four heteroatoms selected from oxygen, sulfur and nitrogen. Unless specified otherwise, the heteroaryl groups may be unsubstituted or substituted with one or more substituents (preferably no more than three substituents) selected from the group of substituents listed below in the definition for "substituted." The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—O—) has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as ($C_1$–$C_6$) alkanoyl (e.g., formyl, acetyl, propionyl, butyryl, valeryl, caproyl, t-butylacetyl, etc.), ($C_3$–$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. Unless indicated otherwise, the acyl group may be unsubstituted or optionally substituted with one of more substituents (typically, one to three substituents) selected from the group of substituents listed below in the definition for "substituted."

The term "substituted" specifically envisions and allows for substitutions that are common in the art. However, it is generally understood by those skilled in the art that the substituents should be selected so as to not adversely affect the pharmacological characteristics of the compound or adversely interfere with the use of the medicament. Those skilled in the art will also appreciate that some substitutions may be inherently unstable and therefore do not form a part of this invention. Suitable substituents for any of the groups defined above include ($C_1$–$C_6$)alkyl, partially or fully saturated ($C_3$–$C_7$)cycloalkyl, ($C_2$–$C_6$)alkenyl, aryl, heteroaryl, partially or fully saturated 3- to 6-membered heterocycle, halo (e.g., chloro, bromo, iodo and fluoro), cyano, hydroxy, ($C_1$–$C_6$)alkoxy, aryloxy, sulfhydryl (mercapto), ($C_1$–$C_6$) alkylthio, arylthio, amino, mono- or di-($C_1$–$C_6$)alkyl amino, quaternary ammonium salts, amino($C_1$–$C_6$)alkoxy, aminocarboxylate (i.e., —NH—C(O)—O—($C_1$–$C_6$)alkyl), N—$C_1$–$C_6$)alkylaminocarboxylate, hydroxy($C_1$–$C_6$)alkylamino, amino($C_1$–$C_6$)alkylthio, cyanoamino, formamido, acylamino (e.g., acetamido and benzamido), N—($C_1$–$C_6$) alkyl-acylamino (e.g., N-methylacetamido), nitro, ($C_1$–$C_6$) carbamyl, keto (oxo), acyl, ($C_1$–$C_6$)alkoxycarbonyl, aryloxycarbonyl, ($C_1$–$C_6$)carboxy, glycolyl, glycyl, hydrazino, guanyl, sulfamyl, sulfonyl, sulfinyl, thio($C_1$–$C_6$)carbonyl, thio($C_1$–$C_6$)carboxy, and combinations thereof. In the case of substituted combinations, such as "substituted aryl ($C_1$–$C_6$)alkyl", either the aryl or the alkyl group may be substituted, or both the aryl and the alkyl groups may be substituted with one or more substituents (typically, one to three substituents except in the case of perhalo substitutions). An aryl substituted carbocyclic or heterocyclic group may be a fused ring (e.g., indanyl, dihydrobenzofuranyl, dihydroindolyl, etc.). A cycloalkyl substituted carbocyclic or heterocyclic group may be a spiro-fused ring.

The term "solvate" refers to a molecular complex of a compound of the present invention with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male and female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The phrase "modulated by a cannabinoid receptor" or "modulation of a cannabinoid receptor" refers to the activation or deactivation of cannabinoid receptors. For example, the ligand (i.e., compound of the present invention) may act as an agonist, partial agonist, inverse agonist, antagonist, partial antagonist, and the like.

The term "antagonist" refers to both full and partial antagonists as well as inverse agonists.

The terms "treating", "treat", or "treatment" embrace both preventative, i.e., prophylactic, and palliative treatment.

The term "compounds of the present invention" (unless specifically identified otherwise) refer to compounds of Formula (I), (IA), (IB), (IC), (ID) prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, New York (1967–1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I illustrates an efficient method for preparing compounds of Formula (I) where L is a carbonyl group or compounds of Formula (IA).

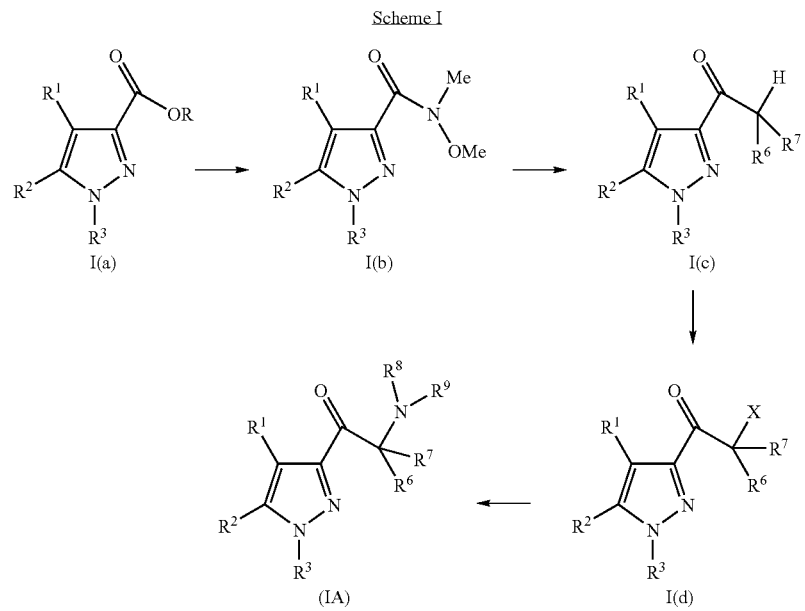

Ester I(a) where $R^2$ and $R^3$ are aryl groups may be prepared using analogous procedures described in U.S. Pat. Nos. 4,944,790, 5,051,518, 5,134,142, and 5,624,941, all of which are incorporated herein by reference, or esterification of the corresponding carboxylic acid prepared by analogous procedures described in Bischler, *Chemische Berichte*, 26, 1881–1890 (1893). Other 1,5-disubstituted aryl and heteroaryl pyrazole ester derivatives may be prepared using analogous procedures.

The amide I(b) is then prepared from the ester I(a) by reacting the ester with N,O-dimethylhydroxylamine hydrochloride and isopropylmagnesium chloride in an aprotic solvent (e.g., THF). The N-methoxyamide I(b) is converted to the ketone I(c) by reacting with $R^6R^7$CH-metal (preferably, magnesium or lithium). The α-haloketone I(d) is prepared using standard halogenation procedures well known to those skilled in the art (e.g., $CuBr_2$ in refluxing ethyl acetate/chloroform). The α-halo group is then displaced with the desired amino group to provide the α-aminoketo compound IA. For example, α-halo intermediate I(d) is reacted with $R^8R^9$NH in the presence of an organic or inorganic base and an aprotic solvent (e.g., diethylisopropylamine and DMSO).

Compound IB' can be easily converted to its corresponding ether IB" (i.e., compounds of Formula (I) where L is —$CR^4(OR^5)$— or compounds of Formula (IB) where $R^4$ is hydrogen or $(C_1-C_6)$alkyl and $R^5$ is $(C_1-C_6)$alkyl) using standard etherization processes well-known to those skilled in the art. For example, treatment of the alcohol IB' with an alkyl halide (e.g., $R^5X$) in the presence of a strong base (e.g., sodium hydride) in an aprotic solvent (e.g., dimethylformamide).

Scheme III below illustrates the preparation of compounds of the present invention where $R^5$ is taken together with either $R^8$ or $R^9$ to form a —$CH_2CH_2$— linkage.

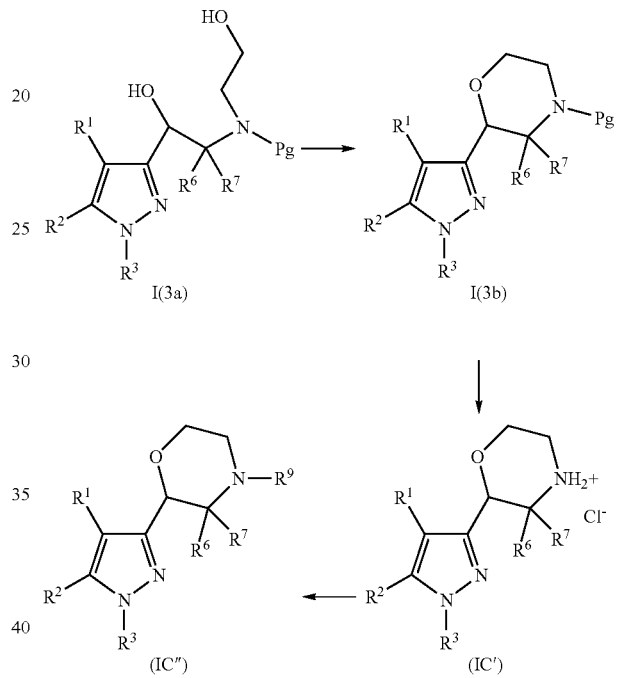

Scheme III

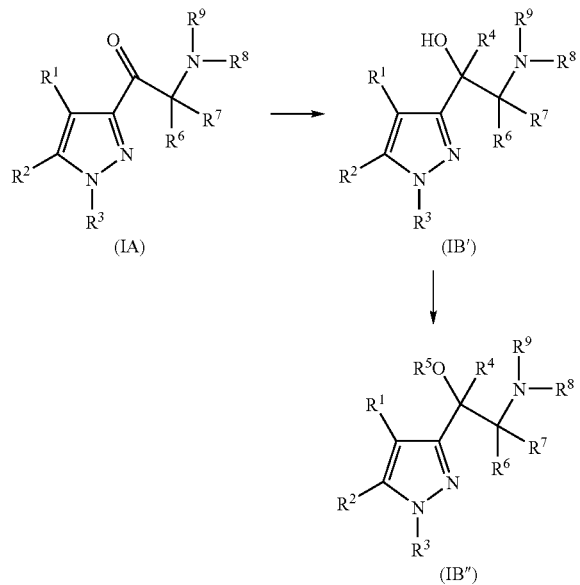

Scheme II

As illustrated in Scheme II above, the compound of Formula (I) where L is a carbonyl group can be converted to a compound of Formula (I) where L is a hydroxymethylene (or a compound of Formula (IB) where $R^4$ and $R^5$ are both hydrogen) by reducing the carbonyl group to its corresponding alcohol. Procedures for reducing ketones to their corresponding alcohols are well-known to those skilled in the art. One convenient method is reduction with sodium borohydride in a protic solvent (e.g., ethanol) to produce a compound of Formula (I) where L is —CH(OH)—. Alternatively, compound IA can be reduced with an organometallic reagent (e.g., lithium or magnesium organometallic, such as $R^4$Li or $R^4$MgBr, dissolved in a nonreactive solvent, typically dry ethyl ether) to produce Compound (IB') (i.e., a compound of Formula (I) where L is —$CR^4$(OH)— or a compound of Formula (IB) where $R^5$ is hydrogen and $R^4$ is $(C_1-C_6)$alkyl).

The N-protected amino compound I(3a) is cyclized to the morpholinyl derivative I(3b) by heating in the presence of a strong acid (e.g. 48% hydrogen bromide). The N-protecting group is then removed by heating in the presence of 1-chloroethyl chloroformate and 1,8-bis(dimethylamino)naphthalene in 1,2-dichloroethane to produce a compound IC' (i.e., a compound of Formula (I) wherein L is —$CH(OR^5)$— or a compound of Formula (IC), where $R^5$ and $R^8$ form an ethylene bridge and $R^9$ is hydrogen). The morpholinyl nitrogen can then be alkylated by treating compound IC' with the appropriate aldehyde/ketone in the presence of sodium triacetoxyborohydride and acetic acid. Alternatively, the morpholinyl nitrogen may be acylated or sulfonated using standard procedures well-known to those skilled in the art. For example, compound IC' may be reacted with $R^{10}(CH_2)_mC(O)Cl$ or $R^{10}(CH_2)_nSO_2Cl$ (where m, n and $R^{10}$ are as defined earlier) in the presence of triethylamine and an aprotic solvent (e.g., dichloromethane). Those compounds where $R^9$ or $R^8$ is —$(CH_2)_pR^{10}$ (where p is 1, 2 or 3 and $R^{10}$ is as defined earlier) may be produced by reducing the carbonyl of the corresponding acylated compound via standard reduction processes well-known to those skilled in the art.

Scheme IV below illustrates the preparation of imidazole derivatives.

using the same general procedures described above for the synthesis of compounds of Formula (IB) and Formula (IC).

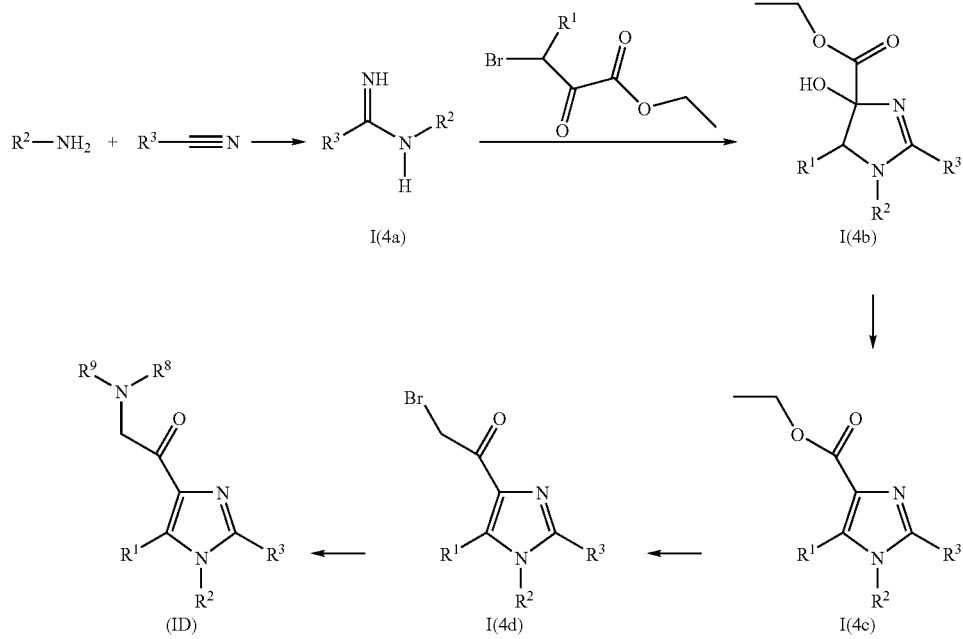

The benzamidine I(4a) is prepared by condensing the desired amine with the desired nitrile. The amine and nitrile are available from a variety of commercial sources or via simple modifications of commercially available materials using procedures well-known to those skilled in the art. One convenient means of achieving the condensation is by pre-treating the amine with trimethylaluminum prior to the addition of the nitrile and then heating the mixture to complete the reaction. The benzamidine I(4a) is then condensed with an appropriately substituted 3-bromo-2-oxo-propionic acid ethyl ester in the presence of a weak base (e.g., sodium bicarbonate) to form the hydroxy ester I(4b). The hydroxy ester I(4b) is then dehydrated to form the imidazole I(4c). The ester group of imidazole I(4c) is converted to the α-bromo ketone I(4d) by saponification of the ester using basic conditions such as lithium hydroxide in a mixture of methanol and water, reacting the intermediate acid with N,O-dimethylhydroxylamine hydrochloride and a suitable coupling agent, such as dicyclohexylcarbodiimide (DCC) or 1-propane phosphonic acid cyclic anhydride in an aprotic solvent (e.g., THF). The intermediate N-methoxyamide is converted to the ketone by reacting with $R^6R^7CH$-metal (preferably, magnesium-halide (Grignard reagent) or lithium). The α-haloketone I(4d) is prepared using standard halogenation procedures well known to those skilled in the art (e.g., $Br_2$ in acetic acid). The α-bromo group can then be displaced with the desired amine to form the desired α-amine ketone (ID). For a more detailed description of the steps outlined in Scheme IV above, see Example 7 below.

Compound (ID) may be converted to imidazole derivatives wherein L is —$C(R^4)(OR^5)$—, where $R^4$ is hydrogen or ($C_1$–$C_6$)alkyl and $R^5$ is hydrogen, ($C_1$–$C_6$)alkyl, or taken together with $R^8$ or $R^9$ is —$CH_2CH_2$— or —$CH_2C(O)$—

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention contains an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N—($C_1$–$C_6$)alkoxycarbonylaminomethyl, succinoyl, ($C_1$–$C_6$)alkanoyl, α-amino ($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$–$C_6$)alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C(OY$_0$)Y$_1$ wherein Y$_0$ is ($C_1$–$C_4$) alkyl and Y$_1$ is ($C_1$–$C_6$) alkyl, carboxy($C_1$–$C_6$)alkyl, amino($C_1$–$C_4$)alkyl or mono-N— or di-N,N—($C_1$–$C_6$)alkylaminoalkyl, —C(Y$_2$)Y$_3$ wherein Y$_2$ is H or methyl and Y$_3$ is mono-N— or di-N,N—($C_1$–$C_6$)alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers resulting from the N-oxidation of the pyrimidine and pyrazine rings are also within the scope of the present invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. For example, all of the tautomeric forms of the imidazole and pyrazole moieties are included in the invention. Also, for example, all keto-enol and imine-enamine forms of the compounds are included in the invention.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, iodine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{123}$I, and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and/or in the Examples hereinbelow, by substituting an isotopically labeled reagent for a non-isotopically labeled reagent.

Compounds of the present invention are useful for treating diseases, conditions and/or disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, a typical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y antagonists, thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine and peptide $YY_{3-36}$ or an analog thereof. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$(including analogs) can be prepared as described in US Publication No. 2002/0141985 and WO 03/027637. All of the above recited references are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; COX-2 inhibitors; antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguamides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: cigliazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-COA synthase inhibitor, or a HMG-COA reductase or synthase gene expression inhibitor, a CETP inhibitor, a bile acid sequesterant, a fibrate, an ACAT inhibitor, a squalene synthetase inhibitor, an antioxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent will also be generally dependent upon a number of factors including the health of the subject being treated, the extent of treatment desired, the nature and kind of concurrent therapy, if any, and the frequency of treatment and the nature of the effect desired. In general, the dosage range of an anti-obesity agent is in the range of from about 0.001 mg to about 100 mg per kilogram body weight of the individual per day, preferably from about 0.1 mg to about 10 mg per kilogram body weight of the individual per day. However, some is variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile condition with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity® 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile:, available from Waters Corp., Milford, Mass.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. MS peaks are reported for all examples. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) under low nitrogen pressure.

Example 1 provides general procedures for preparing compounds of Formula (I) where L is a carbonyl.

Example 1

N-Methoxy-N-methyl-5-(4-chlorophenyl)-1-(2-chlorophenyl)-4-methyl-1H-pyrazole-3-carboxamide (I-1a)

Isopropylmagnesium chloride (15 ml, 30 mmol) was added dropwise over a 10 to 15 minute period to a stirred solution of ethyl 5-(4-chlorophenyl)-1-(2-chlorophenyl)-4-methyl-1H-pyrazole-3-carboxylate (8.15 g, 21.7 mmol) and N,O-dimethylhydroxylamine hydrochloride (1.51 g, 15.5 mmol) in THF at −25° C. After stirring for an additional 15 minutes at −25° C., the reaction mixture was quenched with saturated aqueous NH$_4$Cl and then extracted with methyl-tert-butyl ether. The organic layer was washed with brine, dried over sodium sulfate and concentrated in vacuo to give the title compound I-1a as a golden oil (8.76 g).

1-[5-(4-Chlorophenyl)-1-(2-chlorophenyl)-4-methyl-1H-pyrazol-3-yl]-ethanone(I-1b)

Methylmagnesium bromide (10 ml, 30.4 mmol) was added dropwise to a stirred solution of N-methoxy-N-methyl-5-(4-chlorophenyl)-1-(2-chlorophenyl)-4-methyl-1H-pyrazole-3-carboxamide I-1a (8.48 g, 21.7 mmol) in THF (100 ml) at −10° C. The reaction mixture was stirred for another 15 minutes at −10° C. to afford a yellow solution which became slurry within 30 minutes. The reaction mixture was warmed up to 0° C. over a period of 30 minutes, quenched with NH$_4$Cl and diluted with ethyl acetate. The organic layer was washed with brine, dried over sodium sulfate, and concentrated in vacuo to give the title compound I-1b as a light-yellow colored solid (7.52 g).

2-Bromo-1-[5-(4-chlorophenyl)-1-(2-chlorophenyl)-4-methyl-1H-pyrazol-3-yl]-ethanone(I-1c)

Copper (II) bromide (12.9 g, 58.0 mmol) was added to a solution of 1-[5-(4-chlorophenyl)-1-(2-chlorophenyl)-4-methyl-1H-pyrazol-3-yl]-ethanone I-1b in 1:1 ethyl acetate/methylene chloride (400 ml). The reaction mixture was heated in an oil bath to reflux for 2.5 hours. The reaction was monitored by $^1$HNMR/LCMS. The reaction mixture was removed from the oil bath and filtered through a Celite® pad and then washed with ethyl acetate (1 L). The filtrate was partitioned with 200 ml H$_2$O. The organic layer was separated, dried over sodium sulfate, and concentrated in vacuo. The resulting solids were purified by chromatography (25%–35% methylene chloride/hexanes, silica) to give the title compound I-1c (8.91 g).

General Procedure for the Preparation of a Compound of Formula (I) Where L is —C(O)—.

A solution of 2-bromo-1-[5-(4-chlorophenyl)-1-(2-chlorophenyl)-4-methyl-1H-pyrazol-3-yl]-ethanone I-1c (130 mg, 0.307 mmol) in dichloromethane (1 ml) was treated with the appropriate amine (0.398 mmol) and diisopropylethylamine (70 μL, 0.4 mmol) at room temperature. The reaction mixture was stirred overnight at room temperature and then diluted with methylene chloride, washed with half saturated sodium bicarbonate, dried over magnesium sulfate, and concentrated in vacuo. The residue was purified by silica gel chromatography to afford the appropriate aminoketone.

Table I lists compounds that were prepared using the general procedures described above with the appropriate starting materials.

TABLE I

| Example No. | Compound Name | LCMS m/z (M + 1) |
|---|---|---|
| 1A-1 | 2-(Benzyl-isopropyl-amino)-1-[1-(2-chlorophenyl)-5-(4-chlorophenyl)-4-methyl-1H-pyrazol-3-yl]-ethanone hydrochloride salt | 492.2 |
| 1A-2 | 1-[5-(4-Chlorophenyl)-1-(2-chlorophenyl)-4-methyl-1H-pyrazol-3-yl]-2-[4-(5-trifluoromethyl-pyridin-2-yl)-piperazin-1-yl]-ethanone formate salt | 574.1 |
| 1A-3 | 1-[5-(4-chlorophenyl)-1-(2-chlorophenyl)-4-methyl-1H-pyrazol-3-yl]-2-(2,6-dimethyl-morpholin-4-yl)-ethanone formate salt | 457.9 |
| 1A-4 | 1-{2-[1-(2-Chlorophenyl)-5-(4-chlorophenyl)-4-methyl-1H-pyrazol-3-yl]-2-oxo-ethyl}-4-phenyl-piperidine-4-carbonitrile formate salt | 529.1 |
| 1A-5 | 2-(4-Acetyl-4-phenyl-piperidin-1-yl)-1-[1-(2-chlorophenyl)-5-(4-chlorophenyl)-4-methyl-1H-pyrazol-3-yl]-ethanone formate salt | 546.1 |
| 1A-6 | 1-[5-(4-Chlorophenyl)-1-(2-chlorophenyl)-4-methyl-1H-pyrazol-3-yl]-2-(3,3-dimethylpiperidin-1-yl)-ethanone formate salt | 456.0 |
| 1A-7 | 1-[1-(2-Chlorophenyl)-5-(4-chlorophenyl)-4-methyl-1H-pyrazol-3-yl]-2-(2,6-dimethylpiperidin-1-yl)-ethanone formate salt | 456.1 |
| 1A-8 | 1-[5-(4-Chlorophenyl)-1-(2-chlorophenyl)-4-methyl-1H-pyrazol-3-yl]-2-[4-(3-trifluoromethylpyridin-2-yl)-piperazin-1-yl]-ethanone formate salt | 574.1 |
| 1A-9 | 2-(4-Benzyl-[1,4]diazepan-1-yl)-1-[1-(2-chlorophenyl)-5-(4-chlorophenyl)-4-methyl-1H-pyrazol-3-yl]-ethanone formate salt | 532.9 |

TABLE I-continued

| Example No. | Compound Name | LCMS m/z (M + 1) |
|---|---|---|
| 1A-10 | 1-[1-(2-Chlorophenyl)-5-(4-chlorophenyl)-4-methyl-1H-pyrazol-3-yl]-2-(2-methoxymethyl-pyrrolidin-1-yl)-ethanone formate salt | 458.1 |
| 1A-11 | 1-[1-(2-Chlorophenyl)-5-(4-chlorophenyl)-4-methyl-1H-pyrazol-3-yl]-2-(2-oxa-5-aza-bicyclo[2.2.1]hept-5-yl)-ethanone formate salt | 442.1 |
| 1A-12 | 1-[1-(2-chlorophenyl)-5-(4-chlorophenyl)-4-methyl-1H-pyrazol-3-yl]-2-(ethyl-[1,3,4]thiadiazol-2-yl-amino)-ethanone formate salt | 458.5 |
| 1A-13 | 1-[5-(4-chlorophenyl)-1-(2-chlorophenyl)-4-methyl-1H-pyrazol-3-yl]-2-[3-(3-methoxy-phenyl)-piperidin-1-yl]-ethanone | 534.1 |
| 1A-14 | 1-[1-(2-chlorophenyl)-5-(4-chlorophenyl)-4-methyl-1H-pyrazol-3-yl]--(3-hydroxy-3-o-tolyl-pyrrolidin-1-yl)-ethanone | 520.1 |
| 1A-15 | 1-[5-(4-chlorophenyl)-1-(2-chlorophenyl)-4-methyl-1H-pyrazol-3-yl]-2-[4-(4-methyl-4H-[1,2,4]triazol-3-yl)-piperidin-1-yl]-ethanone. | 509.1 |
| 1A-16 | 1-[5-(4-chlorophenyl)-1-(2-chlorophenyl)-4-methyl-1H-pyrazol-3-yl]-2-[4-(3,4-dihydro-1H-isoquinolin-2-yl)-piperidin-1-yl]-ethanone | 559.2 |
| 1A-17 | 1-[1-(2-chlorophenyl)-5-(4-chlorophenyl)-4-methyl-1H-pyrazol-3-yl]-2-(4-hydroxy-4-phenyl-octahydro-quinolin-1-yl)-ethanone | 574.1 |
| 1A-18 | 1-[5-(4-chlorophenyl)-1-(2-chlorophenyl)-4-methyl-1H-pyrazol-3-yl]--(4-trifluoromethyl-10-aza-tricyclo[6.3.1.0]dodeca-2,4,6-trien-10-yl)-ethanone | 570.0 |
| 1A-19 | 1-[5-(4-chlorophenyl)-1-(2-chlorophenyl)-4-methyl-1H-pyrazol-3-yl]-2-[methyl-(5-phenyl-1H-pyrazol-3-ylmethyl)-amino]-ethanone | 529.1 |
| 1A-20 | 1-[1-(2-chlorophenyl)-5-(4-chlorophenyl)-4-methyl-1H-pyrazol-3-yl]-2-[methyl-(1-pyridin-4-yl-ethyl)-amino]-ethanone | 479.6 |
| 1A-21 | 1-[1-(2-chlorophenyl)-5-(4-chlorophenyl)-4-methyl-1H-pyrazol-3-yl]-2-[methyl-(1-pyridin-3-yl-ethyl)-amino]-ethanone | 479.1 |
| 1A-22 | 1-[1-(2-chlorophenyl)-5-(4-chlorophenyl)-4-methyl-1H-pyrazol-3-yl]-2-(3-phenyl-piperidin-1-yl)-ethanone | 504.2 |
| 1A-23 | 1-[5-(4-chlorophenyl)-1-(2-chlorophenyl)-4-methyl-1H-pyrazol-3-yl]-2-(4-pyrimidin-2-yl-[1,4]diazepan-1-yl)-ethanone | 521.1 |
| 1A-24 | N-(1-{2-[1-(2-chlorophenyl)-5-(4-chlorophenyl)-4-methyl-1H-pyrazol-3-yl]-2-oxo-ethyl}-pyrrolidin-3-yl)-N-methyl-acetamide | 485.7 |
| 1A-25 | 1-[5-(4-chlorophenyl)-1-(2-chlorophenyl)-4-methyl-1H-pyrazol-3-yl]-2-(2,3-dihydro-5H-benzo[f][1,4]oxazepin-4-yl)-ethanone | 492.7 |
| 1A-26 | 1-[5-(4-chlorophenyl)-1-(2-chlorophenyl)-4-methyl-1H-pyrazol-3-yl]-2-[methyl-(1-methyl-1H-pyrazol-4-ylmethyl)-amino]-ethanone | 468.7 |
| 1A-27 | 1-[5-(4-chlorophenyl)-1-(2-chlorophenyl)-4-methyl-1H-pyrazol-3-yl]-2-(1,1-dioxo-thiazolidin-3-yl)-ethanone | 464.1 |
| 1A-28 | 1-[1-(2-chlorophenyl)-5-(4-chlorophenyl)-4-methyl-1H-pyrazol-3-yl]-2-spiro[isobenzofuran-1(3H),4'-piperidin-1'-yl]-ethanone | 532.1 |
| 1A-29 | 1-[1-(2-chlorophenyl)-5-(4-chlorophenyl)-4-methyl-1H-pyrazol-3-yl]-2-(methyl-pyridin-2-ylmethyl-amino)-ethanone | 465.7 |
| 1A-30 | 1-[5-(4-chlorophenyl)-1-(2-chlorophenyl)-4-methyl-1H-pyrazol-3-yl]-2-({4-[ethyl-(2-hydroxy-ethyl)-amino]-butyl}-methyl-amino)-ethanone | 518.0 |
| 1A-31 | 1-[1-(2-chlorophenyl)-5-(4-chlorophenyl)-4-methyl-1H-pyrazol-3-yl]-2-[3-(3-methoxy-phenyl)-3-propyl-pyrrolidin-1-yl]-ethanone | 562.2 |
| 1A-32 | 1-{2-[1-(2-chlorophenyl)-5-(4-chlorophenyl)-4-methyl-1H-pyrazol-3-yl]-2-oxo-ethyl}-4-phenyl-piperidine-4-carbonitrile hydrochloride salt | 528.9 |
| 1A-33 | 1-[5-(4-chlorophenyl)-1-(2-chlorophenyl)-4-methyl-1H-pyrazol-3-yl]-2-(3,3-dimethyl-piperidin-1-yl)-ethanone hydrochloride salt | 456.0 |
| 1A-34 | 1-[5-(4-chlorophenyl)-1-(2,4-dichlorophenyl)-4-methyl-1H-pyrazol-3-yl]-2-(3,3-dimethylpiperidin-1-yl)-ethanone | 489.9 |
| 1A-35 | 1-{2-[5-(4-chlorophenyl)-1-(2,4-dichlorophenyl)-4-methyl-1H-pyrazol-3-yl]-2-oxo-ethyl}-4-phenyl-piperidine-4-carbonitrile | 562.8 |
| 1A-36 | 1-{2-[5-(4-chlorophenyl)-1-(2-fluoro-phenyl)-4-methyl-1H-pyrazol-3-yl]-2-oxo-ethyl}-4-phenyl-piperidine-4-carbonitrile | 512.9 |
| 1A-37 | 1-[5-(4-chlorophenyl)-1-(2-fluoro-phenyl)-4-methyl-1H-pyrazol-3-yl]-2-(3,3-dimethyl-piperidin-1-yl)-ethanone | 440.0 |
| 1A-38 | 1-[5-(4-chlorophenyl)-1-(2-chlorophenyl)-4-methyl-1H-pyrazol-3-yl]-2-(3,3-dimethylpiperidin-1-yl)-2-methyl-propan-1-one | 484.4 |
| 1A-39 | 1-[1-(2-chlorophenyl)-5-(4-chlorophenyl)-4-methyl-1H-pyrazol-3-yl]-2-isopropylamino-2-methyl-propan-1-one | 430.2 |
| 1A-40 | 2-[(1-Benzyl-cyclopentyl)-methyl-amino]-1-[5-(4-chlorophenyl)-1-(2-chlorophenyl)-4-methyl-1H-pyrazol-3-yl]-ethanone | 532.8 |
| 1A-41 | 1-[1-(2-chlorophenyl)-5-(4-chlorophenyl)-4-methyl-1H-pyrazol-3-yl]-2-(5-methyl-1,3,4,5-tetrahydro-pyrido[4,3-b]indol-2-yl)-ethanone | 528.8 |
| 1A-42 | 1-[1-(2-chlorophenyl)-5-(4-chlorophenyl)-4-methyl-1H-pyrazol-3-yl]-2-[isopropyl-(2-phenoxy-ethyl)-amino]-ethanone | 522.8 |
| 1A-43 | 1-[5-(4-chlorophenyl)-1-(2-chlorophenyl)-4-methyl-1H-pyrazol-3-yl]-2-[2-(1H-indol-3-yl)-pyrrolidin-1-yl]-ethanone | 529.8 |
| 1A-44 | 2-(4-Benzoyl-piperazin-1-yl)-1-[5-(4-chlorophenyl)-1-(2-chlorophenyl)-4-methyl-1H-pyrazol-3-yl]-ethanone | 535.5 |
| 1A-45 | 1-[5-(4-chlorophenyl)-1-(2-chlorophenyl)-4-methyl-1H-pyrazol-3-yl]-2-[4-(furan-2-carbonyl)-piperazin-1-yl]-ethanone | 525.5 |
| 1A-46 | 1-[1-(2-chlorophenyl)-5-(4-chlorophenyl)-4-methyl-1H-pyrazol-3-yl]-2-[methyl-(1,2,3,4-tetrahydro-naphthalen-1-yl)-amino]-ethanone | 504.8 |
| 1A-47 | 2-(Benzyl-bicyclo[2.2.1]hept-2-yl-amino)-1-[1-(2-chlorophenyl)-5-(4-chlorophenyl)-4-methyl-1H-pyrazol-3-yl]-ethanone | 544.8 |
| 1A-48 | 1-[5-(4-chlorophenyl)-1-(2-chlorophenyl)-4-methyl-1H-pyrazol-3-yl]-2-(3,5-dimethyl-piperidin-1-yl)-ethanone | 456.8 |
| 1A-49 | 2-(1-Aza-spiro[4.5]dec-1-yl)-1-[1-(2-chlorophenyl)-5-(4-chlorophenyl)-4-methyl-1H-pyrazol-3-yl]-ethanone | 482.8 |
| 1A-50 | 1-[5-(4-chlorophenyl)-1-(2-chlorophenyl)-4-methyl-1H-pyrazol-3-yl]-2-(4-phenyl-piperidin-1-yl)-ethanone | 504.8 |
| 1A-51 | 4-{2-[5-(4-chlorophenyl)-1-(2-chlorophenyl)-4-methyl-1H-pyrazol-3-yl]-2-oxo-ethyl}-piperazine-1-carboxylic acid 2-hydroxy-2-methyl-propyl ester | 545.9 |
| 1A-52 | 1-[5-(4-chlorophenyl)-1-(2-chlorophenyl)-4-methyl-1H-pyrazol-3-yl]-2-[4-(tetrahydro-furan-2-ylmethyl)-piperazin-1-yl]-ethanone | 515.5 |
| 1A-53 | 3-{2-[1-(2-chlorophenyl)-5-(4-chlorophenyl)-4-methyl-1H-pyrazol-3-yl]-2-oxo-ethyl}-2,3,4,4a-tetrahydro-1H-3,9a-diaza-fluoren-9-one | 533.5 |
| 1A-54 | 2-(4-Benzo[d]isothiazol-3-yl-piperazin-1-yl)-1-[5-(4-chlorophenyl)-1-(2-chlorophenyl)-4-methyl-1H-pyrazol-3-yl]-ethanone | 562.8 |
| 1A-55 | 2-[(1-Benzyl-pyrrolidin-3-ylmethyl)-methyl-amino]-1-[5-(4-chlorophenyl)-1-(2-chlorophenyl)-4-methyl-1H-pyrazol-3-yl]-ethanone | 549.5 |
| 1A-56 | 2-(3-Benzylamino-8-aza-bicyclo[3.2.1]oct-8-yl)-1-[1-(2-chlorophenyl)-5-(4-chlorophenyl)-4-methyl-1H-pyrazol-3-yl]-ethanone | 561.5 |
| 1A-57 | 1-[1-(2-chlorophenyl)-5-(4-chlorophenyl)-4-methyl-1H-pyrazol-3-yl]-2-(1-p-tolyl-3-aza-bicyclo[3.1.0]hex-3-yl)-ethanone | 516.8 |
| 1A-58 | 1-[1-(2-chlorophenyl)-5-(4-chlorophenyl)-4-methyl-1H-pyrazol-3-yl]-2-(8-methoxy-3,4-dihydro-1H-isoquinolin-2-yl)-ethanone | 506.8 |
| 1A-59 | 2-[Benzyl-(2-hydroxymethyl-cyclohexyl)-amino]-1-[5-(4-chlorophenyl)-1-(2-chlorophenyl)-4-methyl-1H-pyrazol-3-yl]-ethanone | 562.8 |

TABLE I-continued

| Example No. | Compound Name | LCMS m/z (M + 1) |
|---|---|---|
| 1A-60 | 1-[5-(4-chlorophenyl)-1-(2-chlorophenyl)-4-methyl-1H-pyrazol-3-yl]-2-(3-hydroxymethyl-3,4-dihydro-1H-isoquinolin-2-yl)-ethanone | 506.8 |
| 1A-61 | 2-({2-[5-(4-chlorophenyl)-1-(2-chlorophenyl)-4-methyl-1H-pyrazol-3-yl]-2-oxo-ethyl}-ethyl-amino)-isonicotinonitrile | 490.7 |
| 1A-62 | 1-[5-(4-chlorophenyl)-1-(2-chlorophenyl)-4-methyl-1H-pyrazol-3-yl]-2-[(2,6-dichloro-benzyl)-(3-hydroxypropyl)-amino]-ethanone | 576.8 |
| 1A-63 | 2-[Benzyl-(2-hydroxy-cyclobutyl)-amino]-1-[5-(4-chlorophenyl)-1-(2-chlorophenyl)-4-methyl-1H-pyrazol-3-yl]-ethanone | 520.8 |
| 1A-64 | 2-(4-Benzo[d]isoxazol-3-yl-piperazin-1-yl)-1-[5-(4-chlorophenyl)-1-(2-chlorophenyl)-4-methyl-1H-pyrazol-3-yl]-ethanone | 546.8 |
| 1A-65 | 1-[1-(2-chlorophenyl)-5-(4-chlorophenyl)-4-methyl-1H-pyrazol-3-yl]-2-(3,4-dihydro-6-methoxyspiro[naphthalene-1(2H),4'-piperidin-1'-yl]-ethanone | 574.9 |
| 1A-66 | 1-[5-(4-chlorophenyl)-1-(2-chlorophenyl)-4-methyl-1H-pyrazol-3-yl]-2-[3-(pyrrolidine-1-carbonyl)-piperidin-1-yl]-ethanone | 525.8 |
| 1A-67 | 1-[5-(4-chlorophenyl)-1-(2-chlorophenyl)-4-methyl-1H-pyrazol-3-yl]-2-(3-methyl-3-phenyl-piperidin-1-yl)-ethanone | 536.5 |
| 1A-68 | 1-[5-(4-chlorophenyl)-1-(2-chlorophenyl)-4-methyl-1H-pyrazol-3-yl]-2-[4-(pyridine-4-carbonyl)-piperazin-1-yl]-ethanone | 536.5 |
| 1A-69 | 6-(4-{2-[5-(4-chlorophenyl)-1-(2-chlorophenyl)-4-methyl-1H-pyrazol-3-yl]-2-oxo-ethyl}-piperazin-1-yl)-nicotinonitrile | 531.8 |
| 1A-70 | 5-{2-[5-(4-chlorophenyl)-1-(2-chlorophenyl)-4-methyl-1H-pyrazol-3-yl]-2-oxo-ethyl}-2,5-diaza-bicyclo[2.2.1]heptane-2-carboxylic acid tert-butyl ester | 542.1 |
| 1A-71 | 1-{2-[1-(2-chlorophenyl)-5-(4-chlorophenyl)-4-methyl-1H-pyrazol-3-yl]-2-oxo-ethyl}-4-cyclohexylamino-piperidine-4-carboxylic acid amide | 569.2 |
| 1A-72 | 1-{2-[1-(2-chlorophenyl)-5-(4-chlorophenyl)-4-methyl-1H-pyrazol-3-yl]-2-oxo-ethyl}-4-isopropylamino-piperidine-4-carboxylic acid amide | 530.6 |
| 1A-73 | 1-[5-(4-chlorophenyl)-1-(2-chlorophenyl)-4-methyl-1H-pyrazol-3-yl]-2-(4-pyrimidin-2-yl-piperazin-1-yl)-ethanone | 507.8 |
| 1A-74 | 1-[1-(2-chlorophenyl)-5-(4-chlorophenyl)-4-methyl-1H-pyrazol-3-yl]-2-(methyl-pyridin-4-ylmethyl-amino)-ethanone | 465.7 |
| 1A-75 | 1-[5-(4-chlorophenyl)-1-(2-chlorophenyl)-4-methyl-1H-pyrazol-3-yl]-2-(4-quinoxalin-2-yl-piperazin-1-yl)-ethanone | 557.8 |
| 1A-76 | 1-[5-(4-chlorophenyl)-1-(2-chlorophenyl)-4-methyl-1H-pyrazol-3-yl]-2-[4-(5-chloro-pyridin-2-yl)-piperazin-1-yl]-ethanone | 540.8 |
| 1A-77 | 1-[1-(2-chlorophenyl)-5-(4-chlorophenyl)-4-methyl-1H-pyrazol-3-yl]-2-(10-oxa-4-aza-tricyclo[5.2.1.0]dec-4-yl)-ethanone | 482.8 |
| 1A-78 | 1-[1-(2-chlorophenyl)-5-(4-chlorophenyl)-4-methyl-1H-pyrazol-3-yl]-2-[(1,1-dioxo-tetrahydro-1&-thiophen-3-yl)-methyl-amino]-ethanone | 492.7 |
| 1A-79 | 1-[1-(2-chlorophenyl)-5-(4-chlorophenyl)-4-methyl-1H-pyrazol-3-yl]-2-[(2-hydroxy-1-methyl-2-phenyl-ethyl)-methyl-amino]-ethanone | 508.8 |
| 1A-80 | 1-[5-(4-chlorophenyl)-1-(2-chlorophenyl)-4-methyl-1H-pyrazol-3-yl]-2-(3-hydroxy-piperidin-1-yl)-ethanone | 444.7 |
| 1A-81 | 1-[5-(4-chlorophenyl)-1-(2-chlorophenyl)-4-methyl-1H-pyrazol-3-yl]-2-piperidin-1-yl-ethanone | 428.7 |
| 1A-82 | 1-{2-[1-(2-chlorophenyl)-5-(4-chlorophenyl)-4-methyl-1H-pyrazol-3-yl]-1,1-dimethyl-2-oxo-ethyl}-4-phenyl-piperidine-4-carbonitrile | 557.3 |
| 1A-83 | 1-[5-(4-chlorophenyl)-1-(2-chlorophenyl)-4-methyl-1H-pyrazol-3-yl]-2-cyclohexylamino-ethanone | 442.3 |
| 1A-84 | 2-Benzylamino-1-[5-(4-chlorophenyl)-1-(2-chlorophenyl)-4-methyl-1H-pyrazol-3-yl]-ethanone hydrochloride salt | 450.2 |
| 1A-85 | 1-[5-(4-chlorophenyl)-1-(2-chlorophenyl)-4-methyl-1H-pyrazol-3-yl]-2-[4-(furan-2-carbonyl)-piperazin-1-yl]-ethanone hydrochloride salt | 523.2 |
| 1A-86 | 1-[5-(4-chlorophenyl)-1-(2-chlorophenyl)-4-methyl-1H-pyrazol-3-yl]-2-[4-(4-methyl-4H-[1,2,4]triazol-3-yl)-piperidin-1-yl]-ethanone hydrochloride salt | 509.2 |
| 1A-87 | 1-{2-[1-(2-chlorophenyl)-5-(4-chlorophenyl)-4-methyl-1H-pyrazol-3-yl]-2-oxo-ethyl}-4-isopropylamino-piperidine-4-carboxylic acid amide hydrochloride salt | 528.3 |
| 1A-88 | 1-[5-(4-Chlorophenyl)-1-(2-chlorophenyl)-4-methyl-1H-pyrazol-3-yl]-2-(2-phenylpiperidin-1-yl)-ethanone | 504.9 |
| 1A-89 | 4-{2-[5-(4-Chlorophenyl)-1-(2-chlorophenyl)-4-methyl-1H-pyrazol-3-yl]-2-oxo-ethyl}-piperazine-1-carboxylic acid isobutyl ester | 530.1 |
| 1A-90 | 2-[4-(Benzofuran-2-carbonyl)-piperazin-1-yl]-1-[5-(4-chlorophenyl)-1-(2-chlorophenyl)-4-methyl-1H-pyrazol-3-yl]-ethanone | 573.9 |
| 1A-91 | 1'-{2-[1-(2-Chlorophenyl)-5-(4-chlorophenyl)-4-methyl-1H-pyrazol-3-yl]-2-oxo-ethyl}-[1,4']bipiperidinyl-4'-carboxylic acid amide | 555.2 |
| 1A-92 | 1-[5-(4-chlorophenyl)-1-(2-chlorophenyl)-4-methyl-1H-pyrazol-3-yl]-2-[methyl-(1,2,3,4-tetrahydro-naphthalen-1-ylmethyl)-amino]-ethanone | 518.9 |
| 1A-93 | 3-{2-[1-(2-chlorophenyl)-5-(4-chlorophenyl)-4-methyl-1H-pyrazol-3-yl]-2-oxo-ethyl}-1,2,3,4,5,6-hexahydro-1,5-methano-pyrido[1,2-a][1,5]diazocin-8-one | 533.9 |
| 1A-94 | 1-[5-(4-chlorophenyl)-1-(2-chlorophenyl)-4-methyl-1H-pyrazol-3-yl]-2-[4-(2-phenyl-[1,3]dioxolan-2-yl)-piperidin-1-yl]-ethanone. | 576.9 |
| 1A-95 | 1-[1-(2-chlorophenyl)-5-(4-chlorophenyl)-4-methyl-1H-pyrazol-3-yl]-2-(cyclohexyl-pyridin-4-yl-amino)-ethanone | 519.9 |
| 1A-96 | 1-[1-(2-chlorophenyl)-5-(4-chlorophenyl)-4-methyl-1H-pyrazol-3-yl]-2-[(4-hydroxy-1,1-dioxo-tetrahydro-1-thiophen-3-yl)-isopropyl-amino]-ethanone | 538.6 |
| 1A-97 | (3-{2-[1-(2-chlorophenyl)-5-(4-chlorophenyl)-4-methyl-1H-pyrazol-3-yl]-2-oxo-ethyl}-3-aza-bicyclo[3.1.0]hex-6-yl)-carbamic acid methyl ester | 499.8 |
| 1A-98 | 1-[1-(2-chlorophenyl)-5-(4-chlorophenyl)-4-methyl-1H-pyrazol-3-yl]-2-[4-(4-fluoro-phenyl)-4-hydroxy-piperidin-1-yl]-ethanone | 538.9 |
| 1A-99 | 1-[1-(2-chlorophenyl)-5-(4-chlorophenyl)-4-methyl-1H-pyrazol-3-yl]-2-(3-methyl-3,4-dihydro-1H-isoquinolin-2-yl)-ethanone | 490.8 |
| 1A-100 | 1-[1-(2-chlorophenyl)-5-(4-chlorophenyl)-4-methyl-1H-pyrazol-3-yl]-2-(2,3-dihydrospiro[1H-indene-1,4'-piperinin]-1'-yl-ethanone | 531.2 |
| 1A-101 | 1-[1-(2-chlorophenyl)-5-(4-chlorophenyl)-4-methyl-1H-pyrazol-3-yl]-2-spiro[1H-indene-1,4'-piperinin]-1'-yl-ethanone | 528.9 |
| 1A-102 | 1-[1-(2-chlorophenyl)-5-(4-chlorophenyl)-4-methyl-1H-pyrazol-3-yl]-2-(3-cyclohexyl-piperidin-1-yl)-ethanone | 511.2 |
| 1A-103 | 1-[1-(2-chlorophenyl)-5-(4-chlorophenyl)-4-methyl-1H-pyrazol-3-yl]-2-(3-trifluoromethyl-10-aza-tricyclo[6.3.1.0]dodeca-2(7),3,5-trien-10-yl)-ethanone | 570.8 |
| 1A-104 | 1-[5-(4-chlorophenyl)-1-(2-chlorophenyl)-4-methyl-1H-pyrazol-3-yl]-2-(4-cyclopentyl-piperazin-1-yl)-ethanone | 497.9 |
| 1A-105 | 1-[1-(2-chlorophenyl)-5-(4-chlorophenyl)-4-methyl-1H-pyrazol-3-yl]-2-(3-pyrrol-1-ylmethyl-piperidin-1-yl)-ethanone | 507.9 |
| 1A-106 | 1-[5-(4-chlorophenyl)-1-(2-chlorophenyl)-4-methyl-1H-pyrazol-3-yl]-2-(4-phenyl-azepan-1-yl)-ethanone | 519.1 |

TABLE I-continued

| Example No. | Compound Name | LCMS m/z (M + 1) |
|---|---|---|
| 1A-107 | 1-[1-(2-chlorophenyl)-5-(4-chlorophenyl)-4-methyl-1H-pyrazol-3-yl]-2-[cyclopentyl-(2-hydroxy-ethyl)-amino]-ethanone | 472.8 |
| 1A-108 | 1-[1-(2-chlorophenyl)-5-(4-chlorophenyl)-4-methyl-1H-pyrazol-3-yl]-2-[2-(4-fluoro-phenyl)-pyrrolidin-1-yl]-ethanone | 508.8 |
| 1A-109 | 1-[1-(2-chlorophenyl)-5-(4-chlorophenyl)-4-methyl-1H-pyrazol-3-yl]-2-[2-(2-methyl-pyridin-4-yl)-pyrrolidin-1-yl]-ethanone | 507.5 |
| 1A-110 | (1-{2-[5-(4-chlorophenyl)-1-(2-chlorophenyl)-4-methyl-1H-pyrazol-3-yl]-2-oxo-ethyl}-piperidin-4-yl)-carbamic acid tert-butyl ester | 543.9 |
| 1A-111 | (1-{2-[5-(4-chlorophenyl)-1-(2-chlorophenyl)-4-methyl-1H-pyrazol-3-yl]-2-oxo-ethyl}-piperidin-4-yl)-methyl-carbamic acid tert-butyl ester | 557.9 |
| 1A-112 | 2-(2-Benzyl-piperidin-1-yl)-1-[1-(2-chlorophenyl)-5-(4-chlorophenyl)-4-methyl-1H-pyrazol-3-yl]-ethanone | 518.9 |
| 1A-113 | 2-[Benzyl-(2-hydroxymethyl-cyclohexyl)-amino]-1-[5-(4-chlorophenyl)-1-(2-chlorophenyl)-4-methyl-1H-pyrazol-3-yl]-ethanone | 563.0 |
| 1A-114 | 4-{2-[1-(2-chlorophenyl)-5-(4-chlorophenyl)-4-methyl-1H-pyrazol-3-yl]-2-oxo-ethyl}-[1,4]diazepane-1-carboxylic acid tert-butyl ester | 543.9 |
| 1A-115 | 1-[1-(2-chlorophenyl)-5-(4-chlorophenyl)-4-methyl-1H-pyrazol-3-yl]-2-(1,3-dihydro-isoindol-2-yl)-ethanone | 462.8 |
| 1A-116 | 2-(4-Benzyl-piperidin-1-yl)-1-[5-(4-chlorophenyl)-1-(2-chlorophenyl)-4-methyl-1H-pyrazol-3-yl]-ethanone | 518.9 |
| 1A-117 | 1-[5-(4-chlorophenyl)-1-(2-chlorophenyl)-4-methyl-1H-pyrazol-3-yl]-2-[3-(3,5-dimethyl-pyrazol-1-yl)-4-hydroxy-pyrrolidin-1-yl]-ethanone | 525.1 |
| 1A-118 | 1-[5-(4-chlorophenyl)-1-(2-chlorophenyl)-4-methyl-1H-pyrazol-3-yl]-2-(1,4-dioxa-8-aza-spiro[4.5]dec-8-yl)-ethanone | 487.0 |
| 1A-119 | 1-[1-(2-chlorophenyl)-5-(4-chlorophenyl)-4-methyl-1H-pyrazol-3-yl]-2-[cyclopentyl-(2-methoxy-ethyl)-amino]-ethanone | 486.9 |
| 1A-120 | 1-[5-(4-chlorophenyl)-1-(2-chlorophenyl)-4-methyl-1H-pyrazol-3-yl]-2-(1-methyl-10-oxa-4-aza-tricyclo[5.2.1.0]dec-4-yl)-ethanone | 496.8 |
| 1A-121 | 1-[1-(2-chlorophenyl)-5-(4-chlorophenyl)-4-methyl-1H-pyrazol-3-yl]-2-(2,5-dimethyl-pyrrolidin-1-yl)-ethanone | 442.8 |
| 1A-122 | 4-{2-[5-(4-chlorophenyl)-1-(2-chlorophenyl)-4-methyl-1H-pyrazol-3-yl]-2-oxo-ethyl}-3,5-dimethyl-piperazine-1-sulfonic acid dimethylamide | 564.9 |
| 1A-123 | 2-(4-Benzyl-[1,4]diazepan-1-yl)-1-[1-(2-chlorophenyl)-5-(4-chlorophenyl)-4-methyl-1H-pyrazol-3-yl]-ethanone | 535.6 |
| 1A-124 | 1-[5-(4-chlorophenyl)-1-(2-chlorophenyl)-4-methyl-1H-pyrazol-3-yl]-2-[4-(5-trifluoromethyl-pyridin-2-yl)-piperazin-1-yl]-ethanone | 574.9 |
| 1A-125 | N-(1-{2-[1-(2-chlorophenyl)-5-(4-chlorophenyl)-4-methyl-1H-pyrazol-3-yl]-2-oxo-ethyl}-pyrrolidin-3-yl)-N-methyl-acetamide | 486.1 |
| 1A-126 | 4-{2-[1-(2-chlorophenyl)-5-(4-chlorophenyl)-4-methyl-1H-pyrazol-3-yl]-2-oxo-ethyl}-piperazine-1-sulfonic acid dimethylamide | 537.1 |
| 1A-127 | 1-[1-(2-chlorophenyl)-5-(4-chlorophenyl)-4-methyl-1H-pyrazol-3-yl]-2-(1-ethyl-3,4-dihydro-1H-pyrrolo[1,2-a]pyrazin-2-yl)-ethanone | 494.1 |
| 1A-128 | 1-[5-(4-chlorophenyl)-1-(2-chlorophenyl)-4-methyl-1H-pyrazol-3-yl]-2-[4-(2,6-dimethyl-morpholin-4-yl)-piperidin-1-yl]-ethanone | 543.6 |
| 1A-129 | 1-[5-(4-chlorophenyl)-1-(2-chlorophenyl)-4-methyl-1H-pyrazol-3-yl]-2-[methyl-(2-pyridin-2-yl-ethyl)-amino]-ethanone | 479.8 |
| 1A-130 | 4-(1-{2-[1-(2-chlorophenyl)-5-(4-chlorophenyl)-4-methyl-1H-pyrazol-3-yl]-2-oxo-ethyl}-piperidin-4-yloxy)-2-fluoro-benzonitrile | 563.9 |
| 1A-131 | 2-(4-Acetyl-piperazin-1-yl)-1-[5-(4-chlorophenyl)-1-(2-chlorophenyl)-4-methyl-1H-pyrazol-3-yl]-ethanone | 471.8 |
| 1A-132 | 1-[5-(4-chlorophenyl)-1-(2-chlorophenyl)-4-methyl-1H-pyrazol-3-yl]-2-(2-methyl-7,8-dihydro-5H-pyrido[4,3-d]pyrimidin-6-yl)-ethanone | 492.8 |
| 1A-133 | 1-[1-(2-chlorophenyl)-5-(4-chlorophenyl)-4-methyl-1H-pyrazol-3-yl]-2-(2-cyclopropyl-7,8-dihydro-5H-pyrido[4,3-d]pyrimidin-6-yl)-ethanone | 519.1 |
| 1A-134 | 1-[5-(4-chlorophenyl)-1-(2-chlorophenyl)-4-methyl-1H-pyrazol-3-yl]-2-[4-(6-methoxy-pyridazin-3-yl)-piperazin-1-yl]-ethanone | 537.9 |
| 1A-135 | 1-[5-(4-chlorophenyl)-1-(2-chlorophenyl)-4-methyl-1H-pyrazol-3-yl]-2-[3-(4-methyl-4H-[1,2,4]triazol-3-yl)-piperidin-1-yl]-ethanone | 511.6 |
| 1A-136 | (1-{2-[1-(2-chlorophenyl)-5-(4-chlorophenyl)-4-methyl-1H-pyrazol-3-yl]-2-oxo-ethyl}-4-methyl-piperidin-3-yl)-carbamic acid tert-butyl ester | 558.0 |
| 1A-137 | 1-[1-(2-chlorophenyl)-5-(4-chlorophenyl)-4-methyl-1H-pyrazol-3-yl]-2-(1-methyl-3,4-dihydro-1H-pyrrolo[1,2-a]pyrazin-2-yl)-ethanone | 480.0 |
| 1A-138 | 1-[5-(4-chlorophenyl)-1-(2-chlorophenyl)-4-methyl-1H-pyrazol-3-yl]-2-(4-m-tolyloxy-piperidin-1-yl)-ethanone | 534.9 |
| 1A-139 | 2-[4-(1-{2-[5-(4-chlorophenyl)-1-(2-chlorophenyl)-4-methyl-1H-pyrazol-3-yl]-2-oxo-ethyl}-piperidin-4-yloxy)-phenyl]-acetamide | 577.9 |
| 1A-140 | 1-{2-[5-(4-chlorophenyl)-1-(2-fluoro-phenyl)-4-methyl-1H-pyrazol-3-yl]-2-oxo-ethyl}-4-isopropylamino-piperidine-4-carboxylic acid amide hydrochloride salt | 512.3 |
| 1A-141 | 1-[1-(2-chlorophenyl)-5-(4-chlorophenyl)-4-methyl-1H-pyrazol-3-yl]-2-(4-ethoxy-piperidin-1-yl)-ethanone | 472.8 |
| 1A-142 | 1-[1-(2-chlorophenyl)-5-(4-chlorophenyl)-4-methyl-1H-pyrazol-3-yl]-2-(cyclohexyl-pyridin-2-yl-amino)-ethanone | 519.9 |
| 1A-143 | 4-{2-[5-(4-chlorophenyl)-1-(2-chlorophenyl)-4-methyl-1H-pyrazol-3-yl]-2-oxo-ethyl}-piperazine-1-carboxylic acid tert-butyl ester | 529.2 |
| 1A-144 | 1-[5-(4-chlorophenyl)-1-(2-chlorophenyl)-4-methyl-1H-pyrazol-3-yl]-2-piperazin-1-yl-ethanone hydrochloride salt | 429.2 |
| 1A-145 | 1-{2-[1-(2-chlorophenyl)-5-(4-chlorophenyl)-4-methyl-1H-pyrazol-3-yl]-2-oxo-ethyl}-azetidine-3-carboxylic acid methyl ester | 490.3 |
| 1A-146 | 1-[5-(4-chlorophenyl)-1-(2-fluoro-phenyl)-4-methyl-1H-pyrazol-3-yl]-2-[4-(furan-2-carbonyl)-piperazin-1-yl]-ethanone hydrochloride salt | 507.2 |
| 1A-147 | 1-[5-(4-chlorophenyl)-1-(2-chlorophenyl)-4-methyl-1H-pyrazol-3-yl]-2-(4-cyclopentanecarbonyl-piperazin-1-yl)-ethanone | 525.3 |
| 1A-148 | 1-[5-(4-chlorophenyl)-1-(2-chlorophenyl)-4-methyl-1H-pyrazol-3-yl]-2-[4-(5-methyl-1H-pyrazole-3-carbonyl)-piperazin-1-yl]-ethanone hydrochloride salt | 537.2 |
| 1A-149 | 1-[5-(4-chlorophenyl)-1-(2-chlorophenyl)-4-methyl-1H-pyrazol-3-yl]-2-[4-(pyridine-2-carbonyl)-piperazin-1-yl]-ethanone | 534.3 |
| 1A-150 | 1-[5-(4-chlorophenyl)-1-(2-chlorophenyl)-4-methyl-1H-pyrazol-3-yl]-2-[4-(pyrazine-2-carbonyl)-piperazin-1-yl]-ethanone | 535.2 |
| 1A-151 | 1-[5-(4-chlorophenyl)-1-(2-chlorophenyl)-4-methyl-1H-pyrazol-3-yl]-2-piperidin-1-yl-ethanone. hydrochloride salt | 428.1 |
| 1A-152 | 1-[5-(4-chlorophenyl)-1-(2-chlorophenyl)-4-methyl-1H-pyrazol-3-yl]-2-(4-pyrimidin-2-yl-piperazin-1-yl)-ethanone hydrochloride salt | 507.1 |
| 1A-153 | 2-(4-Benzoyl-piperazin-1-yl)-1-[5-(4-chlorophenyl)-1-(2-chlorophenyl)-4-methyl-1H-pyrazol-3-yl]-ethanone hydrochloride salt | 533.1 |
| 1A-154 | 1-[1-(2-chlorophenyl)-5-(4-chlorophenyl)-4-methyl-1H-pyrazol-3-yl]-2-(4-methanesulfonyl-piperazin-1-yl)-ethanone | 507.1 |
| 1A-155 | 1-[1-(2-chlorophenyl)-5-(4-chlorophenyl)-4-methyl-1H-pyrazol-3-yl]-2-[4-(propane-2-sulfonyl)-piperazin-1-yl]-ethanone | 535.2 |

TABLE I-continued

| Example No. | Compound Name | LCMS m/z (M + 1) |
|---|---|---|
| 1A-156 | 1-[5-(4-chlorophenyl)-1-(2-chlorophenyl)-4-methyl-1H-pyrazol-3-yl]-2-(4-trifluoroacetyl-piperazin-1-yl)-ethanone | 525.2 |
| 1A-157 | 1-[5-(4-chlorophenyl)-1-(2-chlorophenyl)-4-methyl-1H-pyrazol-3-yl]-2-hydroxy-piperidin-1-yl)-ethanone | 444.6 |
| 1A-158 | 1-[5-(4-chlorophenyl)-1-(2-chlorophenyl)-4-methyl-1H-pyrazol-3-yl]-2-morpholin-4-yl-ethanone | 430.2 |
| 1A-159 | 1-{2-[5-(4-chlorophenyl)-1-(2-chlorophenyl)-4-methyl-1H-pyrazol-3-yl]-2-oxo-ethyl}-piperidine-4-carboxylic acid dimethylamide | 499.3 |
| 1A-160 | 1-{2-[5-(4-chlorophenyl)-1-(2-chlorophenyl)-4-methyl-1H-pyrazol-3-yl]-2-oxo-ethyl}-piperidine-4-carboxylic acid ethylamide | 499.3 |
| 1A-161 | 1-{2-[1-(2-chlorophenyl)-5-(4-chlorophenyl)-4-methyl-1H-pyrazol-3-yl]-2-oxo-ethyl}-piperidine-4-carboxylic acid cyclopentylamide | 539.8 |
| 1A-162 | 1-[5-(4-chlorophenyl)-1-(2-chlorophenyl)-4-methyl-1H-pyrazol-3-yl]-2-[4-(3-hydroxymethyl-piperidine-1-carbonyl)-piperidin-1-yl]-ethanone | 569.8 |
| 1A-163 | 1-{2-[5-(4-chlorophenyl)-1-(2-chlorophenyl)-4-methyl-1H-pyrazol-3-yl]-2-oxo-ethyl}-piperidine-4-carboxylic acid amide | 471.7 |
| 1A-164 | 1-(1-{2-[5-(4-chlorophenyl)-1-(2-chlorophenyl)-4-methyl-1H-pyrazol-3-yl]-2-oxo-ethyl}-piperidin-4-yl)-pyrrolidin-2-one | 511.8 |
| 1A-165 | 8-{2-[5-(4-chlorophenyl)-1-(2-chlorophenyl)-4-methyl-1H-pyrazol-3-yl]-2-oxo-ethyl}-1-isopropyl-1,3,8-triaza-spiro[4.5]decan-4-one | 540.8 |
| 1A-166 | 3-(Benzyl-{2-[5-(4-chlorophenyl)-1-(2-chlorophenyl)-4-methyl-1H-pyrazol-3-yl]-2-oxo-ethyl}-amino)-propionitrile | 503.8 |
| 1A-167 | Cyclopentanecarboxylic acid (1-{2-[1-(2-chlorophenyl)-5-(4-chlorophenyl)-4-methyl-1H-pyrazol-3-yl]-2-oxo-ethyl}-piperidin-4-yl)-amide | 539.8 |
| 1A-168 | 2-(4-Acetyl-[1,4]diazepan-1-yl)-1-[1-(2-chlorophenyl)-5-(4-chlorophenyl)-4-methyl-1H-pyrazol-3-yl]-ethanone | 485.8 |
| 1A-169 | 1-[5-(4-chlorophenyl)-1-(2-chlorophenyl)-4-methyl-1H-pyrazol-3-yl]-2-[3-(4-fluoro-phenoxy)-azetidin-1-yl]-ethanone | 510.2 |
| 1A-170 | 1-[1-(2-chlorophenyl)-5-(4-chlorophenyl)-4-methyl-1H-pyrazol-3-yl]-2-[4-(4-trifluoromethyl-pyrimidin-2-yl)-piperazin-1-yl]-ethanone | 575.8 |
| 1A-171 | 4-{2-[1-(2-chlorophenyl)-5-(4-chlorophenyl)-4-methyl-1H-pyrazol-3-yl]-2-oxo-ethyl}-piperazine-1-sulfonic acid dimethylamide hydrochloride salt | 536.2 |
| 1A-172 | 2-(4-Amino-piperidin-1-yl)-1-[5-(4-chlorophenyl)-1-(2-chlorophenyl)-4-methyl-1H-pyrazol-3-yl]-ethanone hydrochloride salt | 443.3 |
| 1A-173 | 4-{2-[5-(4-chlorophenyl)-1-(2-chlorophenyl)-4-methyl-1H-pyrazol-3-yl]-2-oxo-ethyl}-piperazine-1-carboxylic acid isobutyl ester hydrochloride salt | 529.3 |
| 1A-174 | 1-[5-(4-chlorophenyl)-1-(2-chlorophenyl)-4-methyl-1H-pyrazol-3-yl]-2-[4-(thiophene-3-carbonyl)-piperazin-1-yl]-ethanone | 539.1 |
| 1A-175 | 2-(4-{2-[5-(4-chlorophenyl)-1-(2-chlorophenyl)-4-methyl-1H-pyrazol-3-yl]-2-oxo-ethyl}-piperazine-1A-carbonyl)-pyrrolidine-1-carbaldehyde | 554.1 |
| 1A-176 | 1-[5-(4-chlorophenyl)-1-(2-chlorophenyl)-4-methyl-1H-pyrazol-3-yl]-2-[4-(5-methyl-isoxazole-3-carbonyl)-piperazin-1-yl]-ethanone | 538.0 |
| 1A-177 | 1-[1-(2-chlorophenyl)-5-(4-chlorophenyl)-4-methyl-1H-pyrazol-3-yl]-2-(4-ethoxyacetyl-piperazin-1-yl)-ethanone | 515.1 |
| 1A-178 | 1-[5-(4-chlorophenyl)-1-(2-chlorophenyl)-4-methyl-1H-pyrazol-3-yl]-2-[4-(1,5-dimethyl-1H-pyrazole-3-carbonyl)-piperazin-1-yl]-ethanone | 551.1 |
| 1A-179 | 1-[5-(4-chlorophenyl)-1-(2-chlorophenyl)-4-methyl-1H-pyrazol-3-yl]-2-[4-([1,2,3]thiadiazole-4-carbonyl)-piperazin-1-yl]-ethanone | 541.0 |
| 1A-180 | 1-[5-(4-chlorophenyl)-1-(2-chlorophenyl)-4-methyl-1H-pyrazol-3-yl]-2-[4-(5-methyl-isoxazole-4-carbonyl)-piperazin-1-yl]-ethanone | 538.1 |
| 1A-181 | 1-[5-(4-chlorophenyl)-1-(2-chlorophenyl)-4-methyl-1H-pyrazol-3-yl]-2-[4-(thiazole-4-carbonyl)-piperazin-1-yl]-ethanone | 540.0 |
| 1A-182 | 4-(4-{2-[5-(4-chlorophenyl)-1-(2-chlorophenyl)-4-methyl-1H-pyrazol-3-yl]-2-oxo-ethyl}-piperazine-1-carbonyl)-1-methyl-pyrrolidin-2-one | 554.1 |
| 1A-183 | 4-(4-{2-[5-(4-chlorophenyl)-1-(2-chlorophenyl)-4-methyl-1H-pyrazol-3-yl]-2-oxo-ethyl}-piperazine-1-carbonyl)-benzonitrile | 558.1 |
| 1A-184 | 1-[5-(4-chlorophenyl)-1-(2-chlorophenyl)-4-methyl-1H-pyrazol-3-yl]-2-[4-(furan-3-carbonyl)-piperazin-1-yl]-ethanone | 523.2 |
| 1A-185 | 1-[5-(4-chlorophenyl)-1-(2-chlorophenyl)-4-methyl-1H-pyrazol-3-yl]-2-[4-(1-methyl-1H-pyrrole-2-carbonyl)-piperazin-1-yl]-ethanone | 536.1 |
| 1A-186 | 1-[5-(4-chlorophenyl)-1-(2-chlorophenyl)-4-methyl-1H-pyrazol-3-yl]-2-[4-(isoxazole-3-carbonyl)-piperazin-1-yl]-ethanone | 524.1 |
| 1A-187 | 1-[5-(4-chlorophenyl)-1-(2-chlorophenyl)-4-methyl-1H-pyrazol-3-yl]-2-[4-(2-methyl-2H-pyrazole-3-carbonyl)-piperazin-1-yl]-ethanone | 537.1 |
| 1A-188 | 1-[5-(4-chlorophenyl)-1-(2-chlorophenyl)-4-methyl-1H-pyrazol-3-yl]-2-[4-(5-methyl-1H-pyrazole-3-carbonyl)-piperazin-1-yl]-ethanone | 537.1 |
| 1A-189 | 1-[5-(4-chlorophenyl)-1-(2-chlorophenyl)-4-methyl-1H-pyrazol-3-yl]-2-[4-(tetrahydro-furan-2-carbonyl)-piperazin-1-yl]-ethanone | 527.2 |
| 1A-190 | 1-[5-(4-chlorophenyl)-1-(2-chlorophenyl)-4-methyl-1H-pyrazol-3-yl]-2-(4-methoxyacetyl-piperazin-1-yl)-ethanone | 501.1 |
| 1A-191 | 2-[4-(5-Chloro-furan-2-carbonyl)-piperazin-1-yl]-1-[5-(4-chlorophenyl)-1-(2-chlorophenyl)-4-methyl-1H-pyrazol-3-yl]-ethanone | 559.0 |
| 1A-192 | 1-[5-(4-chlorophenyl)-1-(2-chlorophenyl)-4-methyl-1H-pyrazol-3-yl]-2-[4-(isothiazole-4-carbonyl)-piperazin-1-yl]-ethanone | 540.1 |
| 1A-193 | N-[2-(4-{2-[5-(4-chlorophenyl)-1-(2-chlorophenyl)-4-methyl-1H-pyrazol-3-yl]-2-oxo-ethyl}-piperazin-1-yl)-2-oxo-ethyl]-acetamide | 528.1 |
| 1A-194 | 1-[5-(4-chlorophenyl)-1-(2-chlorophenyl)-4-methyl-1H-pyrazol-3-yl]-2-[4-(tetrahydro-pyran-4-carbonyl)-piperazin-1-yl]-ethanone | 541.2 |
| 1A-195 | 1-[5-(4-chlorophenyl)-1-(2-chlorophenyl)-4-methyl-1H-pyrazol-3-yl]-2-{4-[(5-methylpyrazol-1-yl)-acetyl]-piperazin-1-yl}-ethanone | 551.1 |
| 1A-196 | 1-[5-(4-chlorophenyl)-1-(2-chlorophenyl)-4-methyl-1H-pyrazol-3-yl]-2-(4-cyclopropanecarbonyl-piperazin-1-yl)-ethanone | 497.1 |
| 1A-197 | 1-[5-(4-chlorophenyl)-1-(2-chlorophenyl)-4-methyl-1H-pyrazol-3-yl]-2-[4-(1-methyl-cyclopropanecarbonyl)-piperazin-1-yl]-ethanone | 511.1 |
| 1A-198 | 1-[5-(4-chlorophenyl)-1-(2-chlorophenyl)-4-methyl-1H-pyrazol-3-yl]-2-[4-(5-methyl-[1,3,4]oxadiazole-2-carbonyl)-piperazin-1-yl]-ethanone | 539.1 |
| 1A-199 | 5-(4-{2-[5-(4-chlorophenyl)-1-(2-chlorophenyl)-4-methyl-1H-pyrazol-3-yl]-2-oxo-ethyl}-piperazine-1-carbonyl)-pyrrolidin-2-one | 540.1 |
| 1A-200 | N-(1-{2-[5-(4-chlorophenyl)-1-(2-chlorophenyl)-4-methyl-1H-pyrazol-3-yl]-2-oxo-ethyl}-piperidin-4-yl)-2,2,2-trifluoro-acetamide | 539.1 |
| 1A-201 | N-(1-{2-[5-(4-chlorophenyl)-1-(2-chlorophenyl)-4-methyl-1H-pyrazol-3-yl]-2-oxo-ethyl}-piperidin-4-yl)-methanesulfonamide | 521.2 |
| 1A-202 | N-(1-{2-[1-(2-chlorophenyl)-5-(4-chlorophenyl)-4-methyl-1H-pyrazol-3-yl]-2-oxo-ethyl}-piperidin-4-yl)-2-ethoxy-acetamide | 529.3 |
| 1A-203 | 1-Methyl-5-oxo-pyrrolidine-3-carboxylic acid (1-{2-[1-(2-chlorophenyl)-5-(4-chlorophenyl)-4-methyl-1H-pyrazol-3-yl]-2-oxo-ethyl}-piperidin-4-yl)-amide | 568.3 |
| 1A-204 | 5-Methyl-isoxazole-4-carboxylic acid (1-{2-[5-(4-chlorophenyl)-1-(2-chlorophenyl)-4-methyl-1H-pyrazol-3-yl]-2-oxo-ethyl}-piperidin-4-yl)-amide | 552.3 |

TABLE I-continued

| Example No. | Compound Name | LCMS m/z (M + 1) |
|---|---|---|
| 1A-205 | 1-[5-(4-chlorophenyl)-1-(2-chlorophenyl)-4-methyl-1H-pyrazol-3-yl]-2-(4-trifluoroacetyl-piperazin-1-yl)-ethanone hydrochloride salt | 525.2 |
| 1A-206 | 4-{2-[5-(4-chlorophenyl)-1-(2-chlorophenyl)-4-methyl-1H-pyrazol-3-yl]-2-oxo-ethyl}-piperazine-1-carboxylic acid pyrazol-1-ylmethyl ester | 553.3 |
| 1A-207 | Tetrahydro-pyran-4-carboxylic acid (1-{2-[1-(2-chlorophenyl)-5-(4-chlorophenyl)-4-methyl-1H-pyrazol-3-yl]-2-oxo-ethyl}-piperidin-4-yl)-amide | 555.1 |
| 1A-208 | N-(1-{2-[1-(2-chlorophenyl)-5-(4-chlorophenyl)-4-methyl-1H-pyrazol-3-yl]-2-oxo-ethyl}-piperidin-4-yl)-2-(5-methyl-pyrazol-1-yl)-acetamide | 565.2 |
| 1A-209 | 1-[5-(4-chlorophenyl)-1-(2-chlorophenyl)-4-methyl-1H-pyrazol-3-yl]-2-[4-(4-fluoro-benzoyl)-piperazin-1-yl]-ethanone hydrochloride salt | 552.1 |
| 1A-210 | 1-[5-(4-chlorophenyl)-1-(2-chlorophenyl)-4-methyl-1H-pyrazol-3-yl]-2-morpholin-4-yl-ethanone hydrochloride salt | 430.2 |
| 1A-211 | 1-[5-(4-chlorophenyl)-1-(2-fluoro-phenyl)-4-methyl-1H-pyrazol-3-yl]-2-morpholin-4-yl-ethanone hydrochloride salt | 414.3 |
| 1A-212 | 2-(4-Benzoyl-piperazin-1-yl)-1-[5-(4-chlorophenyl)-1-(2-fluoro-phenyl)-4-methyl-1H-pyrazol-3-yl]-ethanone hydrochloride salt | 517.3 |
| 1A-213 | 1-[5-(4-chlorophenyl)-1-(2-fluoro-phenyl)-4-methyl-1H-pyrazol-3-yl]-2-[4-(4-fluoro-benzoyl)-piperazin-1-yl]-ethanone hydrochloride salt | 535.3 |
| 1A-214 | 1-[5-(4-chlorophenyl)-1-(2-fluoro-phenyl)-4-methyl-1H-pyrazol-3-yl]-2-piperidin-1-yl-ethanone hydrochloride salt | 486.3 |
| 1A-215 | 1-[5-(4-chlorophenyl)-1-(2-chlorophenyl)-4-methyl-1H-pyrazol-3-yl]-2-(1,4-dioxa-8-aza-spiro[4.5]dec-8-yl)-ethanone hydrochloride salt | 487.0 |
| 1A-216 | N-(1-{2-[5-(4-chlorophenyl)-1-(2-chlorophenyl)-4-methyl-1H-pyrazol-3-yl]-2-oxo-ethyl}-piperidin-4-yl)-2,2,2-trifluoro-acetamide hydrochloride salt | 539.1 |

Example 2 illustrates the preparation of compounds of Formula (I) where L is —CR$^4$(OR$^5$)—, where R$^4$ and R$^5$ are both hydrogen.

Example 2

2-(Benzyl-isopropyl-amino)-1-[1-(2-chlorophenyl-5-(4-chlorophenyl)-4-methyl-1H-pyrazol-3-yl]-ethanol (2A-1)

To the solution of 2-(benzyl-isopropyl-amino)-1-[5-(4-chlorophenyl)-1-(2-chlorophenyl)-4-methyl-1H-pyrazol-3-yl]-ethanone hydrochloride 1A-1 (250 mg, 0.47 mmol) in 2 ml ethanol was added sodium borohydride (32 mg, 0.71 mmol). The reaction was monitored by TLC (30% ethyl acetate/hexanes). After the completion, the reaction was quenched with water and partitioned between ethyl acetate and saturated NaHCO$_3$. The organic layer was washed with brine, dried over sodium sulfate, and concentrated in vacuo. The product was further purified by chromatography (silica gel, 40% ethyl acetate/hexanes) to give the title compound 2A-1(187 mg).

$^1$H NMR in CD$_2$Cl$_2$ (ppm): δ 7.4–7.1 (m, 13H), 4.71 (d, 1H), 3.9–3.57 (AB quartet, 2H), 3.04 (m, 1H), 2.90–2.77 (AB quartet, 2H), 2.00 (s, 3H), 1.15 (d, 3H), 1.05 (d, 3H). ms (LCMS) m/z=494.2 (M+)

The compounds listed in Table 2 below were prepared using the general procedures described above and the appropriate α-aminoketone compound from Example 1.

TABLE 2

| Example No. | Compound Name | LCMS m/z (M + 1) |
|---|---|---|
| 2A-2 | 2-(Benzyl-isopropyl-amino)-1-[1-(2-chlorophenyl)-5-(4-chlorophenyl)-4-methyl-1H-pyrazol-3-yl]-ethanol hydrochloride salt | 494.2 |
| 2A-3 | 2-[Benzyl-(2-hydroxy-ethyl)-amino]-1-[5-(4-chlorophenyl)-1-(2-chlorophenyl)-4-methyl-1H-pyrazol-3-yl]-ethanol | 496.1 |
| 2A-4 | 1-Benzylamino-1-[5-(4-chlorophenyl)-1-(2-chlorophenyl)-4-methyl-1H-pyrazol-3-yl]-ethanol hydrochloride salt | 452.1 |
| 2A-5 | 1-[5-(4-Chlorophenyl)-1-(2-chlorophenyl)-4-methyl-1H-pyrazol-3-yl]-2-(2,6-dimethyl-morpholin-4-yl)-ethanol | 460.2 |
| 2A-6 | 1-[5-(4-Chlorophenyl)-1-(2-chlorophenyl)-4-methyl-1H-pyrazol-3-yl]-2-[4-(3-trifluoromethyl-pyridin-2-yl)-piperazin-1-yl]-ethanol | 576.1 |
| 2A-7 | 1-[5-(4-Chlorophenyl)-1-(2-chlorophenyl)-4-methyl-1H-pyrazol-3-yl]-2-[4-(5-trifluoromethyl-pyridin-2-yl)-piperazin-1-yl]-ethanol | 576.0 |
| 2A-8 | 1-{2-[1-(2-Chlorophenyl)-5-(4-chlorophenyl)-4-methyl-1H-pyrazol-3-yl]-2-hydroxy-ethyl}-4-phenyl-piperidine-4-carbonitrile | 531.1 |
| 2A-9 | 1-[1-(2-Chlorophenyl)-5-(4-chlorophenyl)-4-methyl-1H-pyrazol-3-yl]-2-[4-(1-hydroxy-ethyl)-4-phenyl-piperidin-1-yl]-ethanol | 550.1 |
| 2A-10 | 1-[5-(4-Chlorophenyl)-1-(2-chlorophenyl)-4-methyl-1H-pyrazol-3-yl]-2-(3,3-dimethyl-piperidin-1-yl)-ethanol | 458.1 |
| 2A-11 | 1-[1-(2-Chlorophenyl)-5-(4-chlorophenyl)-4-methyl-1H-pyrazol-3-yl]-2-(2-methoxymethyl-pyrrolidin-1-yl)-ethanol | 460.1 |
| 2A-12 | 1-[1-(2-Chlorophenyl)-5-(4-chlorophenyl)-4-methyl-1H-pyrazol-3-yl]-2-(2-oxa-5-aza-bicyclo[2.2.1]hept-5-yl)-ethanol | 444.1 |
| 2A-13 | 1-[1-(2-Chlorophenyl)-5-(4-chlorophenyl)-4-methyl-1H-pyrazol-3-yl]-2-(ethyl-[1,3,4]thiadiazol-2-yl-amino)-ethanol | 474.0 |
| 2A-14 | 1-[5-(4-Chlorophenyl)-1-(2-chlorophenyl)-4-methyl-1H-pyrazol-3-yl]-2-[3-(3-methoxy-phenyl)-piperidin-1-yl]-ethanol | 536.8 |
| 2A-14 | 1-{2-[1-(2-Chlorophenyl)-5-(4-chlorophenyl)-4-methyl-1H-pyrazol-3-yl]-2-hydroxy-ethyl}-3-o-tolyl-pyrrolidin-3-ol | 522.8 |
| 2A-15 | 1-[5-(4-Chlorophenyl)-1-(2-chlorophenyl)-4-methyl-1H-pyrazol-3-yl]-2-[4-(4-methyl-4H-[1,2,4]triazol-3-yl)-piperazin-1-yl]-ethanol | 511.8 |
| 2A-16 | 1-[5-(4-Chlorophenyl)-1-(2-chlorophenyl)-4-methyl-1H-pyrazol-3-yl]-2-[4-(3,4-dihydro-1H-isoquinolin-2-yl)-piperidin-1-yl]-ethanol | 561.1 |
| 2A-17 | 1-{2-[1-(2-Chlorophenyl)-5-(4-chlorophenyl)-4-methyl-1H-pyrazol-3-yl]-2-hydroxy-ethyl}-4-phenyl-decahydroquinolin-4-ol | 576.9 |
| 2A-18 | 1-[5-(4-Chlorophenyl)-1-(2-chlorophenyl)-4-methyl-1H-pyrazol-3-yl]-2-(4-trifluoromethyl-10-aza-tricyclo[6.3.1.0]dodeca-2,4,6-trien-10-yl)-ethanol | 572.8 |
| 2A-19 | 1-[1-(2-Chlorophenyl)-5-(4-chlorophenyl)-4-methyl-1H-pyrazol-3-yl]-2-(3-phenyl-piperidin-1-yl)-ethanol | 506.8 |
| 2A-20 | N-(1-{2-[1-(2-Chlorophenyl)-5-(4-chlorophenyl)-4-methyl-1H-pyrazol-3-yl]-2-hydroxy-ethyl}-pyrrolidin-3-yl)-N-methyl-acetamide | 486.9 |
| 2A-21 | 1-[5-(4-Chlorophenyl)-1-(2-chlorophenyl)-4-methyl-1H-pyrazol-3-yl]-2-(2,3-dihydro-5H-benzo[f][1,4]oxazepin-4-yl)-ethanol | 494.8 |
| 2A-22 | 1-[5-(4-Chlorophenyl)-1-(2-chlorophenyl)-4-methyl-1H-pyrazol-3-yl]-2-[methyl-(1-methyl-1H-pyrazol-4-ylmethyl)-amino]-ethanol | 470.1 |
| 2A-23 | α-[1-(2-chlorophenyl)-5-(4-chlorophenyl)-4-methyl-1H-pyrazol-3-yl]-spiro[isobenzofuran-1(3H),4'piperidine]-1'-ethanol | 534.8 |
| 2A-24 | 1-[1-(2-Chlorophenyl)-5-(4-chlorophenyl)-4-methyl-1H-pyrazol-3-yl]-2-(methyl-pyridin-2-ylmethyl-amino)-ethanol | 467.7 |
| 2A-24 | 1-[1-(2-Chlorophenyl)-5-(4-chlorophenyl)-4-methyl-1H-pyrazol-3-yl]-2-[3-(3-methoxy-phenyl)-3-propyl-pyrrolidin-1-yl]-ethanol | 564.9 |

TABLE 2-continued

| Example No. | Compound Name | LCMS m/z (M + 1) |
|---|---|---|
| 2A-25 | 1-{2-[1-(2-Chlorophenyl)-5-(4-chlorophenyl)-4-methyl-1H-pyrazol-3-yl]-2-hydroxy-ethyl}-4-phenyl-piperidine-4-carbonitrile hydrochloride salt | 530.9 |
| 2A-26 | 1-[5-(4-Chlorophenyl)-1-(2-chlorophenyl)-4-methyl-1H-pyrazol-3-yl]-2-(3,3-dimethyl-piperidin-1-yl)-ethanol hydrochloride salt | 458.1 |
| 2A-27 | 1-[5-(4-Chlorophenyl)-1-(2,4-dichlorophenyl)-4-methyl-1H-pyrazol-3-yl]-2-(3,3-dimethyl-piperidin-1-yl)-ethanol | 492.1 |
| 2A-28 | 1-{2-[5-(4-Chlorophenyl)-1-(2,4-dichlorophenyl)-4-methyl-1H-pyrazol-3-yl]-2-hydroxy-ethyl}-4-phenyl-piperidine-4-carbonitrile | 565.1 |
| 2A-29 | 1-[5-(4-Chlorophenyl)-1-(2-chlorophenyl)-4-methyl-1H-pyrazol-3-yl]-2-(3,3-dimethyl-piperidin-1-yl)-2-methyl-propan-1-ol | 486.3 |
| 2A-30 | 1-[1-(2-Chlorophenyl)-5-(4-chlorophenyl)-4-methyl-1H-pyrazol-3-yl]-2-isopropylamino-2-methyl-propan-1-ol | 432.3 |
| 2A-31 | 1-{2-[5-(4-Chlorophenyl)-1-(2-fluoro-phenyl)-4-methyl-1H-pyrazol-3-yl]-2-hydroxy-ethyl}-4-phenyl-piperidine-4-carbonitrile | 515.2 |
| 2A-32 | 1-[5-(4-Chlorophenyl)-1-(2-fluoro-phenyl)-4-methyl-1H-pyrazol-3-yl]-2-(3,3-dimethyl-piperidin-1-yl)-ethanol | 442.3 |
| 2A-33 | 1-{2-[1-(2-Chlorophenyl)-5-(4-chlorophenyl)-4-methyl-1H-pyrazol-3-yl]-2-hydroxy-1,1-dimethyl-ethyl}-4-phenyl-piperidine-4-carbonitrile | 559.3 |
| 2A-34 | (4-{2-[5-(4-Chlorophenyl)-1-(2-chlorophenyl)-4-methyl-1H-pyrazol-3-yl]-2-hydroxy-ethyl}-piperazin-1-yl)-phenyl-methanone | 535.9 |
| 2A-35 | (4-{2-[5-(4-Chlorophenyl)-1-(2-chlorophenyl)-4-methyl-1H-pyrazol-3-yl]-2-hydroxy-ethyl}-piperazin-1-yl)-furan-2-yl-methanone | 525.9 |
| 2A-36 | 2-(Benzyl-bicyclo[2.2.1]hept-2-yl-amino)-1-[1-(2-chlorophenyl)-5-(4-chlorophenyl)-4-methyl-1H-pyrazol-3-yl]-ethanol | 547.0 |
| 2A-37 | 1-[5-(4-Chlorophenyl)-1-(2-chlorophenyl)-4-methyl-1H-pyrazol-3-yl]-2-(3,5-dimethyl-piperidin-1-yl)-ethanol | 458.9 |
| 2A-38 | 1-[5-(4-Chlorophenyl)-1-(2-chlorophenyl)-4-methyl-1H-pyrazol-3-yl]-2-(4-phenyl-piperidin-1-yl)-ethanol | 506.2 |
| 2A-39 | 4-{2-[5-(4-Chlorophenyl)-1-(2-chlorophenyl)-4-methyl-1H-pyrazol-3-yl]-2-hydroxy-ethyl}-piperazine-1-carboxylic acid 2-hydroxy-2-methyl-propyl ester | 547.9 |
| 2A-40 | 1-[5-(4-Chlorophenyl)-1-(2-chlorophenyl)-4-methyl-1H-pyrazol-3-yl]-2-[4-(tetrahydro-furan-2-ylmethyl)-piperazin-1-yl]-ethanol | 515.9 |
| 2A-41 | 3-{2-[1-(2-Chlorophenyl)-5-(4-chlorophenyl)-4-methyl-1H-pyrazol-3-yl]-2-hydroxy-ethyl}-2,3,4,4a-tetrahydro-1H-3,9a-diaza-fluoren-9-one | 533.9 |
| 2A-42 | 2-[(1-Benzyl-pyrrolidin-3-ylmethyl)-methyl-amino]-1-[5-(4-chlorophenyl)-1-(2-chlorophenyl)-4-methyl-1H-pyrazol-3-yl]-ethanol | 551.6 |
| 2A-43 | 2-(3-Benzylamino-8-aza-bicyclo[3.2.1]oct-8-yl)-1-[1-(2-chlorophenyl)-5-(4-chlorophenyl)-4-methyl-1H-pyrazol-3-yl]-ethanol | 563.6 |
| 2A-44 | 1-[1-(2-Chlorophenyl)-5-(4-chlorophenyl)-4-methyl-1H-pyrazol-3-yl]-2-(1-p-tolyl-3-aza-bicyclo[3.1.0]hex-3-yl)-ethanol | 518.9 |
| 2A-45 | 1-[1-(2-Chlorophenyl)-5-(4-chlorophenyl)-4-methyl-1H-pyrazol-3-yl]-2-(8-methoxy-3,4-dihydro-1H-isoquinolin-2-yl)-ethanol | 508.9 |
| 2A-46 | 2-[Benzyl-(2-hydroxymethyl-cyclohexyl)-amino]-1-[5-(4-chlorophenyl)-1-(2-chlorophenyl)-4-methyl-1H-pyrazol-3-yl]-ethanol | 565.0 |
| 2A-47 | 1-[5-(4-Chlorophenyl)-1-(2-chlorophenyl)-4-methyl-1H-pyrazol-3-yl]-2-(3-hydroxymethyl-3,4-dihydro-1H-isoquinolin-2-yl)-ethanol | 508.9 |
| 2A-48 | 3-[{2-[5-(4-Chlorophenyl)-1-(2-chlorophenyl)-4-methyl-1H-pyrazol-3-yl]-2-hydroxy-ethyl}-(2,6-dichloro-benzyl)-amino]-propan-1-ol | 579.2 |
| 2A-49 | 2-(Benzyl-{2-[5-(4-chlorophenyl)-1-(2-chlorophenyl)-4-methyl-1H-pyrazol-3-yl]-2-hydroxy-ethyl}-amino)-cyclobutanol | 522.9 |
| 2A-50 | α-[1-(2-chlorophenyl)-5-(4-chlorophenyl)-4-methyl-1H-pyrazol-3-yl]-3,4-dihydro-6-methoxy-spiro[naphthalene-1(2H),4'piperidine]-1'-ethanol | 577.0 |
| 2A-51 | (1-{2-[5-(4-Chlorophenyl)-1-(2-chlorophenyl)-4-methyl-1H-pyrazol-3-yl]-2-hydroxy-ethyl}-piperidin-3-yl)-pyrrolidin-1-yl-methanone | 527.9 |
| 2A-52 | 1-[5-(4-Chlorophenyl)-1-(2-chlorophenyl)-4-methyl-1H-pyrazol-3-yl]-2-(3-methyl-3-phenyl-piperidin-1-yl)-ethanol | 521.2 |
| 2A-53 | (4-{2-[5-(4-Chlorophenyl)-1-(2-chlorophenyl)-4-methyl-1H-pyrazol-3-yl]-2-hydroxy-ethyl}-piperazin-1-yl)-pyridin-4-yl-methanone | 538.6 |
| 2A-54 | 6-(4-{2-[5-(4-Chlorophenyl)-1-(2-chlorophenyl)-4-methyl-1H-pyrazol-3-yl]-2-hydroxy-ethyl}-piperazin-1-yl)-nicotinonitrile | 534.2 |
| 2A-55 | 1-{2-[1-(2-Chlorophenyl)-5-(4-chlorophenyl)-4-methyl-1H-pyrazol-3-yl]-2-hydroxy-ethyl}-4-cyclohexylamino-piperidine-4-carboxylic acid amide | 572.6 |
| 2A-56 | 1-{2-[1-(2-Chlorophenyl)-5-(4-chlorophenyl)-4-methyl-1H-pyrazol-3-yl]-2-hydroxy-ethyl}-4-isopropylamino-piperidine-4-carboxylic acid amide | 531.2 |
| 2A-57 | 1-[5-(4-Chlorophenyl)-1-(2-chlorophenyl)-4-methyl-1H-pyrazol-3-yl]-2-(4-pyrimidin-2-yl-piperazin-1-yl)-ethanol | 507.9 |
| 2A-58 | 1-[1-(2-Chlorophenyl)-5-(4-chlorophenyl)-4-methyl-1H-pyrazol-3-yl]-2-(methyl-pyridin-4-ylmethyl-amino)-ethanol | 468.0 |
| 2A-59 | 1-[5-(4-Chlorophenyl)-1-(2-chlorophenyl)-4-methyl-1H-pyrazol-3-yl]-2-[4-(5-chloro-pyridin-2-yl)-piperazin-1-yl]-ethanol | 543.1 |
| 2A-60 | 1-[1-(2-Chlorophenyl)-5-(4-chlorophenyl)-4-methyl-1H-pyrazol-3-yl]-2-[(1,1-dioxo-tetrahydro-1&-thiophen-3-yl)-methyl-amino]-ethanol | 494.8 |
| 2A-61 | 2-({2-[1-(2-Chlorophenyl)-5-(4-chlorophenyl)-4-methyl-1H-pyrazol-3-yl]-2-hydroxy-ethyl}-methyl-amino)-1-phenyl-propan-1-ol | 510.9 |
| 2A-62 | 1-{2-[5-(4-Chlorophenyl)-1-(2-chlorophenyl)-4-methyl-1H-pyrazol-3-yl]-2-hydroxy-ethyl}-piperidin-3-ol | 446.8 |
| 2A-63 | 1-[5-(4-Chlorophenyl)-1-(2-chlorophenyl)-4-methyl-1H-pyrazol-3-yl]-2-piperidin-1-yl-ethanol hydrochloride salt | 430.3 |

Example 3 illustrates the preparation of ether derivatives (i.e., L=—CR$^4$(OR$^5$)—) from the corresponding alcohol (L=—CR$^4$(OH)—) from Example 2.

Example 3

Benzyl-{2-[1-(2-chlorophenyl)-5-(4-chlorophenyl)-4-methyl-1H-pyrazol-3-yl]-2-methoxy-ethyl}-iso-propyl-amine(3A-1)

To the solution of 2-(benzyl-isopropyl-amino)-1-[1-(2-chlorophenyl)-5-(4-chlorophenyl)-4-methyl-1H-pyrazol-3-yl]-ethanol 2A-1 (50 mg, 0.1 mmol) in 0.2 ml DMF was added sodium hydride (5 mg, 0.125 mmol, 60% w/w). After it was stirred for 1 hour, the reaction mixture was cooled to 0° C. Methyl iodide (15 mg, 0.11 mmol) was added and the reaction mixture was then warmed up to room temperature. Stirring was continued for another 2 hours. The reaction mixture was partitioned with ethyl acetate and water. The organic layer was washed with brine, dried over sodium sulfate and concentrated in vacuo. The residue was purified by chromatography (silica gel, 30% ethyl acetate/hexanes) to give the title compound 3A-1 as a white waxy solid (27 mg).

¹H NMR in CD₂Cl₂ (ppm): δ7.4–7.05 (m, 13H); 4.42 (t, 1H); 3.40–3.56 (AB quartet, 2H); 3.26 (s, 3H); 3.01–2.87 (m, 3H); 1.99 (s, 3H); 1.00 (d, 3H); 0.96 (d, 3H);
ms (LCMS) m/z=508.2 (M+1)

Example 4 illustrates the conversion of an α-aminoketone of the present invention (L=—C(O)—) to its corresponding alcohol having a R⁴ group other than hydrogen (i.e., L=—CR⁴(OH)—).

Example 4

1-(Benzyl-isopropyl-amino)-2-[1-(2-chlorophenyl)-5-(4-chlorophenyl)-4-methyl-1H-pyrazol-3-yl]-propan-2-ol (4A-1)

Methyl magnesium bromide (0.1 ml, 0.144 mmol) was added dropwise into the solution of 2-(benzyl-isopropyl-amino)-1-[5-(4-chlorophenyl)-1-(2-chlorophenyl)-4-methyl-1H-pyrazol-3-yl]-ethanone (61 mg, 0.12 mmol) in 0.5 ml THF at room temperature. After 2 h, the reaction mixture was then partitioned with ethyl acetate and saturated NH₄Cl. The organic layer was washed with brine, dried over sodium sulfate and concentrated in vacuo. The residue was purified by chromatography (silica gel, 30% ethyl acetate/hexanes) to give the title compound 4A-1 as a white waxy solid (24 mg).
¹H NMR in CD₂Cl₂ (ppm): δ7.4–6.95 (m, 13H); 3.75–3.55 (AB quartet, 2H); 3.23–2.65 (AB quartet, 2H); 2.90 (m, 1H); 2.16 (s, 3H); 1.50 (s, 3H); 1.05 (d, 3H); 0.98 (d, 3H);
ms (LCMS) m/z=508.2 (M+1)

Example 5 illustrates the preparation of compounds of the present invention where L is —CR⁴(OR⁵)—, where R⁵ and either R⁸ or R⁹ form an ethylene bridge.

Example 5

4-Benzyl-2-[5-(4-chlorophenyl)-1-(2-chlorophenyl)-4-methyl-1H-pyrazol-3-yl]-morpholine (5A-1)

The suspension of 2-[benzyl-(2-hydroxy-ethyl)-amino]-1-[5-(4-chlorophenyl)-1-(2-chlorophenyl)-4-methyl-1H-pyrazol-3-yl]-ethanol 2A-3 (150 mg, 0.3 mmol) in 48% hydrobromic acid (0.3 ml) was heated to 100° C. for 2 hours. After the reaction was complete, the reaction mixture was cooled to room temperature and partitioned with ethyl acetate and saturated NaHCO₃. The organic layer was washed with brine, dried over sodium sulfate and concentrated in vacuo. The residue was purified by chromatography (silica gel, 40% ethyl acetate/hexanes) to give the title compound 5A-1 (77 mg).
¹H NMR in CD₂Cl₂ (ppm): δ7.42–7.13 (m, 3H); 4.76 (d, 1H); 3.98 (d, 1H); 3.82 (t, 1H); 3.60 (s, 2H); 2.97 (d, 1H); 2.80 (d, 1H); 2.54 (t, 1H); 2.32 (t, 1H); 2.10 (s, 3H);
ms (LCMS) m/z=478.1 (M+1)

2-[1-(2-Chlorophenyl)-5-(4-chlorophenyl)-4-methyl-1H-pyrazol-3-yl]-morpholine hydrochloride (5A-2)

The solution of 4-benzyl-2-[5-(4-chlorophenyl)-1-(2-chlorophenyl)-4-methyl-1H-pyrazol-3-yl]-morpholine 5A-1 (840 mg, 1.7 mmol), 1-chloroethyl chloroformate (0.2 ml, 1.87 mmol), and 1,8-bis(dimethylamino)naphthalene (72 mg, 0.34 mmol) in 5 ml 1,2-dichloroethane was heated to 50° C. for 3 hours. The reaction mixture was then cooled to room temperature and concentrated in vacuo. The residue was dissolved in 5 ml MeOH and heated to reflux for 2 hours. After the reaction was completed, the reaction mixture was cooled to room temperature and concentrated. The residue was stirred in 5 ml diethyl ether and the product was precipitated and collected by filtration to give the title compound 5A-2 as a white solid (525 mg).
¹H NMR in CD₃OD (ppm): δ7.45–7.36 (m, 4H); 7.30 (d, 2H); 7.15 (d, 2H); 4.71 (d, 1H); 3.95 (d, 1H); 3.78 (t, 1H); 3/20–2.82 (m, 4H);
ms (LCMS) m/z=388.1 (M+1)

2-[5-(4-Chlorophenyl)-1-(2-chlorophenyl)-4-methyl-1H-pyrazol-3-yl]-4-cyclohexyl-morpholine (5A-3)

Triethyl amine (37 μl, 0.27 mmol) was added into the solution of 2-[1-(2-chlorophenyl)-5-(4-chlorophenyl)-4-methyl-1H-pyrazol-3-yl]-morpholine hydrochloride 5A-2 (75 mg, 0.18 mmol) and cyclohexanone (18 μl, 0.18 mmol) in 0.5 ml 1,2-dichloroethane. The reaction mixture was then treated with sodium triacetoxyborohydride (52 mg, 0.25 mmol) followed by acetic acid at room temperature. Upon the completion of the reaction, the reaction mixture was partitioned with ethyl acetate and saturated NaHCO₃. The organic layer was washed with brine, dried over sodium sulfate, and concentrated in vacuo. The residue was purified by chromatography (silica, 60% ethyl acetate/hexanes) to give the title compound 5A-3 as a white solid (40 mg).
¹H NMR in CD₃OD (ppm): δ7.43–7.38 (m, 4H); 7.30 (d, 2H); 7.17 (d, 2H); 4.00 (d, 1H); 3.80 (t, 1H); 3.05 (d, 1H); 2.84 (d, 1H); 2.72 (t, 1H); 2.54 (t, 1H); 2.35 (m, 1H); 2.13 (s, 3H); 2.00–1.25 (m, 10H);
ms (LCMS) m/z=470.1 (M+1)

The compounds listed in Table 3 below were prepared using the general procedures described above for the preparation of compounds 5A-1, 5A-2 and 5A-3.

TABLE 3

| Example No. | Compound Name | LCMS m/z (M + 1) |
|---|---|---|
| 5A-4 | 2-[1-(2-Chlorophenyl)-5-(4-chlorophenyl)-4-methyl-1H-pyrazol-3-yl]-4-isopropyl-morpholine | 430.1 |
| 5A-5 | 2-[5-(4-Chlorophenyl)-1-(2-chlorophenyl)-4-methyl-1H-pyrazol-3-yl]-4-(tetrahydro-pyran-4-yl)-morpholine | 471.9 |
| 5A-6 | 2-[1-(2-Chlorophenyl)-5-(4-chlorophenyl)-4-methyl-1H-pyrazol-3-yl]-4-(6-methyl-pyridin-2-ylmethyl)-morpholine | 493.3 |
| 5A-7 | 2-[1-(2-Chlorophenyl)-5-(4-chlorophenyl)-4-methyl-1H-pyrazol-3-yl]-4-(4-trifluoromethyl-benzyl)-morpholine | 546.3 |
| 5A-8 | 4-{2-[1-(2-Chlorophenyl)-5-(4-chlorophenyl)-4-methyl-1H-pyrazol-3-yl]-morpholin-4-ylmethyl}-quinoline | 529.2 |
| 5A-9 | 5-Chloro-2-{2-[5-(4-chlorophenyl)-1-(2-chlorophenyl)-4-methyl-1H-pyrazol-3-yl]-morpholin-4-ylmethyl}-1H-indole | 553.2 |
| 5A-10 | 2-[1-(2-Chlorophenyl)-5-(4-chlorophenyl)-4-methyl-1H-pyrazol-3-yl]-4-(5-methyl-2-phenyl-oxazol-4-ylmethyl)-morpholine hydrochloride salt | 559.5 |

Example 6 illustrates compounds of the present invention where either R⁸ or R⁹ is an acyl group or sulfonate group.

Example 6

2-[5-(4-Chlorophenyl)-1-(2-chlorophenyl)-4-methyl-1H-pyrazol-3-yl]-4-(propane-2-sulfonyl)-morpholine (6A-1)

To a stirred suspension of 2-[1-(2-chlorophenyl)-5-(4-chlorophenyl)-4-methyl-1H-pyrazol-3-yl]-morpholine hydrochloride 5A-2 (75 mg, 0.18 mmol) and triethylamine (49 μL, 0.36 mmol) in dichloromethane (0.5 ml) was added isopropylsulfonyl chloride (0.22 μL 0.2 mmol) dropwise. After stirring for 18 h, the reaction was partitioned between ethyl acetate and saturated sodium bicarbonate. The organic layer was washed with brine, dried over sodium sulfate and concentrated in vacuo. The residue was purified by chromatography (silica, 40–50% ethyl acetate/hexanes) to give the title compound 6A-1 as a colorless foam (49 mg).

$^1$H NMR in CD$_3$OD (ppm): δ7.43–7.38 (m, 4H); 7.30 (d, 2H); 7.15 (d, 2H); 4.70 (d, 1H); 4.05 (d, 1H); 3.84–3.17 (m, 6H); 2.15 (s, 3H); 1.36 (d, 6H).

ms (LCMS) m/z=494.1 (M+1).

The compounds listed below in Table 4 were prepared using the general procedures described above with the appropriate acid halide or sulfonyl halide.

TABLE 4

| Example No. | Compound Name | LCMS m/z (M + 1) |
|---|---|---|
| 6A-2 | 2-[5-(4-Chlorophenyl)-1-(2-chlorophenyl)-4-methyl-1H-pyrazol-3-yl]-4-(toluene-4-sulfonyl)-morpholine | 542.1 |
| 6A-3 | {2-[5-(4-Chlorophenyl)-1-(2-chlorophenyl)-4-methyl-1H-pyrazol-3-yl]-morpholin-4-yl}-phenyl-methanone | 492.1 |
| 6A-4 | 1-{2-[1-(2-Chlorophenyl)-5-(4-chlorophenyl)-4-methyl-1H-pyrazol-3-yl]-morpholin-4-yl}-2-methyl-propan-1-one | 458.1 |

Example 7 illustrates the preparation of the imidazole derivatives as outlined in Scheme IV above.

Example 7

Preparation of 2,4-dichloro-N-(4-chloro-phenyl)-benzamidine (I-7a)

Trimethylaluminum (2M in toluene, 111.3 ml, 222.6 mmol) was added dropwise to a solution of 4-chlorophenylamine (20 g, 156.8 mmol) in toluene (700 ml) at 0° C. over a 70 minute period under N$_2$. The reaction mixture was warmed to room temperature and stirred for 3.5 hours. A solution of benzonitrile (32.4 g, 188.1 mmol) in toluene (100 ml) was added and the reaction mixture was heated to 85° C. overnight, during which time it became homogeneous. The reaction mixture was then cooled to room temperature and poured over a slurry of silica gel in chloroform/methanol (2:1). After filtration, the residue was washed with a mixture of methylene chloride/methanol (2:1). The combined filtrates were concentrated in vacuo, and the resulting yellow solid was triturated with hexanes/ether (2:1). The yellowish solid 2,4-dichloro-N-(4-chlorophenyl)-benzamidine I-7a (34.15 g, 73%) was used in the next reaction without further purification.

Preparation of 1-(4-Chloro-phenyl)-2-(2,4-dichloro-phenyl)-4-hydroxy-4,5-dihydro-1H-imidazole-4-carboxylic acid ethyl ester (I-7b)

A mixture of 2,4-dichloro-N-(4-chloro-phenyl)-benzamidine I-7a (34 g, 113.5 mmol) and sodium bicarbonate (19.1 g, 227 mmol) in 2-propanol (600 ml) was treated with 3-bromo-2-oxo-propionic acid ethyl ester (20 ml, 158.9 mmol). The reaction mixture was heated to 85° C. overnight, and the solvent was removed in vacuo. The residue was partitioned between methylene chloride and water, and the layers were separated. The organic phase was dried over anhydrous magnesium sulfate and concentrated. The residue was triturated with ether/hexanes (1:3), and the yellow solid, 1-(4-chloro-phenyl)-2-(2,4-dichloro-phenyl)-4-hydroxy-4,5-dihydro-1H-imidazole-4-carboxylic acid ethyl ester I-7b (45 g, 96%), was collected by filtration.

Preparation of 1-(4-Chloro-phenyl)-2-(2,4-dichloro-phenyl)-1H-imidazole-4-carboxylic acid ethyl ester (I-7c)

A mixture of 1-(4-chloro-phenyl)-2-(2,4-dichloro-phenyl)-4-hydroxy-4,5-dihydro-1H-imidazole-4-carboxylic acid ethyl ester I-7b (45 g, 108.8 mmol) and p-toluenesulfonic acid monohydrate (2.1 g, 10.8 mmol) in toluene (540 ml) was heated to reflux overnight. The reaction mixture was cooled and the solvent removed in vacuo. The crude residue was taken up in methylene chloride and washed with water, aqueous sodium bicarbonate, and brine. After drying over anhydrous magnesium sulfate and concentrating, the residue was purified by plug filtration on 600 g silica gel using ethyl acetate/hexanes (20:80) to give pure 1-(4-chloro-phenyl)-2-(2,4-dichloro-phenyl)-1H-imidazole-4-carboxylic acid ethyl ester I-7c (30 g, 69.7%).

Preparation of 1-(4-Chloro-phenyl)-2-(2,4-dichloro-phenyl)-1H-imidazole-4-carboxylic acid (I-7d)

A solution of LiOH (6.36 g, 152 mmol) was added to a suspension of 1-(4-chloro-phenyl)-2-(2,4-dichloro-phenyl)-1H-imidazole-4-carboxylic acid ethyl ester I-7c (30 g, 75.8 mmol) in methanol (380 ml). The reaction mixture was heated to reflux for 1 h and then cooled to room temperature. Most of the solvent was removed in vacuo, and the residue was diluted with water and acidified with 3N HCl. The red-brown precipitate was collected by filtration and triturated with 100 ml ethyl acetate/hexanes (20:80) to afford 1-(4-chloro-phenyl)-2-(2,4-dichloro-phenyl)-1H-imidazole-4-carboxylic acid I-7d (26.3 g, 94%) as a pale yellow solid.

Preparation of 1-(4-Chloro-phenyl)-2-(2,4-dichloro-phenyl)-1H-imidazole-4-carboxylic acid methoxy-methyl-amide (I-7e)

To a solution of 1-(4-chloro-phenyl)-2-(2,4-dichloro-phenyl)-1H-imidazole-4-carboxylic acid I-7d (1.31 g, 3.57 mmol) and N,O-dimethylhydroxylamine hydrochloride (0.42 g, 1.2 equiv) in THF (14 ml) were added TEA (4.97 ml, 10 equiv) and 1-propane phosphonic acid cyclic anhydride (3.21 ml, 1.5 equiv). The reaction mixture was stirred at room temperature overnight, diluted with ethyl acetate and washed with water, 10% citric acid, and saturated aqueous sodium chloride. The organic phase was dried over anhydrous magnesium sulfate and concentrated to a foam which was purified by flash column chromatography (silica, 70:30 ethyl acetate/hexane grading to ethyl acetate) to give 1-(4-chloro-phenyl)-2-(2,4-dichloro-phenyl)-1H-imidazole-4-carboxylic acid methoxy-methyl-amide I-7e (485 mg, 33%).

Preparation of 1-[1-(4-Chloro-phenyl)-2-(2,4-dichloro-phenyl)-1H-imidazol-4-yl]-ethanone (I-7f)

A solution of 1-(4-chloro-phenyl)-2-(2,4-dichloro-phenyl)-1H-imidazole-4-carboxylic acid methoxy-methyl-amide I-7e (1.64 g, 3.99 mmol) in THF (16 ml) was cooled to 0° C., and methylmagnesium iodide (4.4 ml of a 3.0 M solution in Et$_2$O, 9.9 mmol) was added dropwise via syringe. The resultant solution was stirred at 0° C. for 1 h, and then the reaction mixture was poured into cold 1N HCl (100 ml). The mixture was extracted with ethyl acetate (2 85-ml portions), and the combined extracts were washed with saturated aqueous sodium chloride (100 ml). The organics were dried over anhydrous magnesium sulfate and were concentrated to afford 1-[1-(4-chloro-phenyl)-2-(2,4-dichloro-phenyl)-1H-imidazol-4-yl]-ethanone I-7f (1.41 g, 97%) that was used in the next reaction without any further purification.

Preparation of 2-Bromo-1-[1-(4-chloro-phenyl)-2-(2,4-dichloro-phenyl)-1H-imidazol-4-yl]-ethanone (I-7g)

Aqueous HBr (0.98 ml of a 48% solution) was added to a solution of 1-[1-(4-chloro-phenyl)-2-(2,4-dichloro-phenyl)-1H-imidazol-4-yl]-ethanone I-7f (1.60 g, 4.38 mmol) in acetic acid (20 ml). Bromine (0.226 ml, 4.38 mmol) was added next to the reaction mixture in a dropwise manner. The resultant orange solution was stirred at 23° C. for 1 h before warming to 40° C. for 40 min and then cooling to 23° C. for 60 h. The reaction mixture was poured into a mixture of ice and saturated aqueous sodium bicarbonate, and the resultant mixture was extracted with ethyl acetate (2 200-ml portions). The combined organics were washed with saturated aqueous sodium bicarbonate (100 ml) and were dried over anhydrous magnesium sulfate and concentrated to afford 2-bromo-1-[1-(4-chloro-phenyl)-2-(2,4-dichloro-phenyl)-1H-imidazol-4-yl]-ethanone I-7g (1.03 g, 53%).

Preparation of 1-[1-(4-Chloro-phenyl)-2-(2,4-dichloro-phenyl)-1H-imidazol-4-yl]-2-morpholin-4-yl-ethanone (7A-1)

Morpholine (0.04 ml, 0.426 mmol) was added to a solution of 2-bromo-1-[1-(4-chloro-phenyl)-2-(2,4-dichloro-phenyl)-1H-imidazol-4-yl]-ethanone I-7g (63 mg, 0.142 mmol) in THF (3 ml). The resultant solution was stirred at 23° C. for 12 hours, diluted with 50 ml methyl tert-butyl ether, and washed with 25 ml water. The organic phase was dried over anhydrous magnesium sulfate and concentrated. The residue was co-evaporated with hexanes once to afford 1-[1-(4-chloro-phenyl)-2-(2,4-dichloro-phenyl)-1H-imidazol-4-yl]-2-morpholin-4-yl-ethanone 7A-1 (52 mg, 81%) as a solid.

ms (LCMS) m/z=450.2 (M+1). $^1$H NMR in $CD_3OD$ (ppm): δ8.3 (s, 1H); 7.56 (d, 1H); 7.50 (d, 2H); 4.72 (m, 3H); 7.24 (d, 1H); 3.89 (s, 2H); 3.74 (t, 4H); 2.64 (m, 4H).

The compounds listed below in Table 5 were prepared using the general procedures described above for the preparation of Example 7A-1.

TABLE 5

| Example No. | Compound Name | LCMS m/z (M + 1) |
|---|---|---|
| 7A-2 | 1-[1-(4-Chloro-phenyl)-2-(2,4-dichloro-phenyl)-1H-imidazol-4-yl]-2-(4-ethyl-piperazin-1-yl)-ethanone | 477.3 |
| 7A-3 | 1-[1-(4-Chloro-phenyl)-2-(2,4-dichloro-phenyl)-1H-imidazol-4-yl]-2-piperidin-1-yl-ethanone | 448.3 |
| 7A-4 | 1-[1-(4-Chloro-phenyl)-2-(2,4-dichloro-phenyl)-1H-imidazol-4-yl]-2-pyrrolidin-1-yl-ethanone | 434.2 |
| 7A-5 | 1-[1-(4-Chloro-phenyl)-2-(2,4-dichloro-phenyl)-1H-imidazol-4-yl]-5-methyl-1H-imidazol-4-yl]-2-piperidin-1-yl-ethanone | 464.5 |

TABLE 5-continued

| Example No. | Compound Name | LCMS m/z (M + 1) |
|---|---|---|
| 7A-6 | 1-[1-(4-Chloro-phenyl)-2-(2,4-dichloro-phenyl)-5-methyl-1H-imidazol-4-yl]-2-morpholin-4-yl-ethanone | 464.5 |

PHARMACOLOGICAL TESTING

The utility of the compounds of the present invention in the practice of the instant invention can be evidenced by activity in at least one of the protocols described hereinbelow. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N',N'-tetraacetic acid
GDP—guanosine diphosphate
sc—subcutaneous
po—orally
ip—intraperitoneal
icv—intra cerebro ventricular
iv—intravenous
[$^3$H]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.
[$^3$H] 5-(1,1-dimethyl-heptyl )-2-[5-hydroxy-2-(3-hydroxy-propyl)-cyclohexyl]-phenol available from NEN Life Science Products, Boston, Mass.
AM251—N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. Those compounds having an activity <20 nM were then tested in the CB-1 GTPγ [$^{35}$S] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" *Current Medicinal Chemistry*, 6, 635–664 (1999) and in WO 92/02640 (U.S. application Ser. No. 07/564,075 filed Aug. 8, 1990, incorporated herein by reference).

The following assays were designed to detect compounds that inhibit the binding of [$^3$H] SR141716A (selective radiolabeled CB-1 ligand) and [$^3$H] 5-(1,1-dimethylheptyl)-2-[5-hydroxy-2-(3-hydroxypropyl)-cyclohexyl]-phenol; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM $MgCl_2$, and 1 mM EDTA) per brain used. A protein assay was performed and 200 µl of tissue totaling 20 µg was added to the assay.

The test compounds were diluted in drug buffer (0.5% BSA, 10% DMSO and TME) and then 25 µl were added to a deep well polypropylene plate. [$^3$H] SR141716A was diluted in a ligand buffer (0.5% BSA plus TME) and 25 µl were added to the plate. A BCA protein assay was used to determine the appropriate tissue concentration and then 200 µl of rat brain tissue at the appropriate concentration was added to the plate. The plates were covered and placed in an incubator at 20° C. for 60 minutes. At the end of the incubation period 250 µl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM $MgCl_2$ and 1 mM EDTA). A protein assay was performed and 200 µl of tissue totaling 20 µg was added to the assay.

The test compounds were diluted in drug buffer (0.5% BSA, 10% DMSO and TME) and then 25 µl were added to a deep well polypropylene plate. [$^3$H] SR141716A was diluted in a ligand buffer (0.5% BSA plus TME) and 25 µl were added to the plate. The plates were covered and placed in an incubator at 30° C. for 60 minutes. At the end of the incubation period 250 µl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

An activity range from 0.1 to 100 nanomolar was observed for the compounds listed in Examples 1 through 7. As a specific example, a binding affinity of 79 nanomolar was observed for the compound of Example 5A-6. Example 5A-6 was chosen for illustrative purposes only and does not imply that the compound of Example 5A-6 is a preferred compound.

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 µl of tissue totaling 10 µg was added to the assay.

The test compounds were diluted in drug buffer (0.5% BSA, 10% DMSO, and 80.5% TME) and then 25 µl were added to the deep well polypropylene plate. [$^3$H] 5-(1,1-Dimethyl-heptyl)-2-[5-hydroxy-2-(3-hydroxy-propyl)-cyclohexyl]-phenol was diluted a ligand buffer (0.5% BSA and 99.5% TME) and then 25 µl were added to each well at a concentration of 1 nM. A BCA protein assay was used to determine the appropriate tissue concentration and 200 µl of the tissue at the appropriate concentration was added to the plate. The plates were covered and placed in an incubator at 30° C. for 60 minutes. At the end of the incubation period 250 µl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S] Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology*, 50, 709–715 (1996). GTPγ [$^{35}$S] binding assays were performed in a 96 well FlashPlate™ format in duplicate using 100 pM GTPγ [$^{35}$S] and 10 µg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 µM GDP, 0.1% bovine serum albumin and the following protease inhibitors: 100 µg/ml bacitracin, 100 µg/ml benzamidine, 5 µg/ml aprotinin, 5 µg/ml leupeptin. The assay mix was then incubated with increasing concentrations of antagonist ($10^{-10}$ M to $10^{-5}$ M) for 10 minutes and challenged with the cannabinoid agonist 5-(1,1-dimethyl-heptyl)-2-[5-hydroxy-2-(3-hydroxy-propyl)-cyclohexyl]-phenol (10 µM). Assays were performed at 30° C. for one hour. The FlashPlates™ were then centrifuged at 2000×g for 10 minutes. Stimulation of GTPγ[$^{35}$S] binding was then quantified using a Wallac Microbeta. $EC_{50}$ calculations done using Prism™ by Graphpad.

Inverse agonism was measured in the absense of agonist.

CB-1 FLIPR-based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 µM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 s period. Compound additions were made simultaneously to all 384 wells after 20 s of baseline. Assays were performed in triplicate and 6 point concentration-response curves generated. Antagonist compounds were subsequently challenged with 31 μM WIN 55,212–2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000–14,000 cells per well at a concentration of 100 μl per well. The plates were incubated for 24 hours in a 37° C. incubator. The media was removed and media lacking serum (100 μl) was added. The plates were then incubated for 18 hours at 37° C.

Serum free medium containing 1 mM IBMX was added to each well followed by 10 μl of test compound (1:10 stock solution (25 mM compound in DMSO) into 50% DMSO/PBS) diluted 10× in PBS with 0.1% BSA. After incubating for 20 minutes at 37° C., 2 μM of Forskolin was added and then incubated for an additional 20 minutes at 37° C. The media was removed, 100 μl of 0.01 N HCl was added and then incubated for 20 minutes at room temperature. Cell lysate (75 μl) along with 25 μl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as $\Delta^9$-tetrahydrocannabinol ($\Delta^9$-THC) and 5-(1,1-dimethyl-heptyl)-2-[5-hydroxy-2-(3-hydroxy-propyl)-cyclohexyl]-phenol have been shown to affect four characteristic behaviors in mice, collectively known as the Tetrad. For a description of these behaviors see: Smith, P. B., et al. in "The pharmacological activity of anandamide, a putative endogenous cannabinoid, in mice." J. Pharmacol. Exp. Ther., 270(1), 219–227 (1994) and Wiley, J., et al. in "Discriminative stimulus effects of anandamide in rats," Eur. J. Pharmacol., 276(1–2), 49–54 (1995). Reversal of these activities in the Locomotor Activity, Catalepsy, Hypothermia, and Hot Plate assays described below provides a screen for in vivo activity of CB-1 antagonists.

All data is presented as % reversal from agonist alone using the following formula: (test compound/agonist—vehicle/agonist)/(vehicle/vehicle—vehicle/agonist). Negative numbers indicate a potentiation of the agonist activity or non-antagonist activity. Positive numbers indicate a reversal of activity for that particular test.

Locomotor Activity

Male ICR mice (n=6) (17–19 g, Charles River Laboratories, Inc., Wilmington, Mass.) were pre-treated with test compound (sc, po, ip, or icv). Fifteen minutes later, the mice were challenged with 5-(1,1-dimethyl-heptyl)-2-[5-hydroxy-2-(3-hydroxy-propyl)-cyclohexyl]-phenol (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6)(17–19 g upon arrival) were pre-treated with test compound (sc, po, ip or icv). Fifteen minutes later, the mice were challenged with 5-(1,1-dimethyl-heptyl)-2-[5-hydroxy-2-(3-hydroxy-propyl)-cyclohexyl]-phenol (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5) (17–19 g upon arrival) were pre-treated with test compounds (sc, po, ip or icv). Fifteen minutes later, mice were challenged with the cannabinoid agonist 5-(1,1-dimethyl-heptyl)-2-[5-hydroxy-2-(3-hydroxy-propyl)-cyclohexyl]-phenol (sc). Sixty-five minutes post agonist injection, rectal body temperatures were taken. This was done by inserting a small thermostat probe approximately 2–2.5 cm into the rectum. Temperatures were recorded to the nearest tenth of a degree Hot Plate Male ICR mice (n=7) (17–19 g upon arrival) are pre-treated with test compounds (sc, po, ip or iv). Fifteen minutes later, mice were challenged with a cannabinoid agonist 5-(1,1-dimethyl-heptyl)-2-[5-hydroxy-2-(3-hydroxy-propyl)-cyclohexyl]-phenol (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow. They were maintained on a 12 hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li ,T. -K., et al., "Indiana selection studies on alcohol related behaviors" in *Development of Animal Models as Pharmacogenetic Tools* (eds McCleam C. E., Deitrich R. A. and Erwin V. G.), Research Monograph 6, 171–192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, New York, 537–544 (1977); and Lumeng, L, et al., "Different sensitivities to ethanol in alcohol-preferring and -nonpreferring rats," *Pharmacol, Biochem Behav.*, 16, 125–130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g. 5.6 mg/kg AM251; n=8); Group 3—low dose test compound (n=8); and Group 4—high dose of test compound (n=8). Test compounds were generally mixed into a vehicle of 30% (w/v) β-cyclodextrin in distilled water at a volume of 1–2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57BI/6 mice (Charles River). Several studies have shown that this strain of mice will readily consume alcohol with little to no manipulation required (Middaugh et al., "Ethanol Consumption by C57BL6 Mice: Influence of Gender and Procedural Variables" *Alcohol*, 17 (3), 175–183, 1999; Le et al., "Alcohol Consumption by C57BL6, BALA/c, and DBA/2 Mice in a Limited Access Paradigm" *Pharmacology Biochemisrty and Behavior*, 47, 375–378, 1994).

For our purposes, upon arrival (17–19 g) mice were individually housed and given unlimited access to powdered rat chow, water and a 10% (w/v) alcohol solution. After 2–3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7–10) so that all groups had equivocal alcohol intake. On day 2 and 3, mice were injected with vehicle or drug and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300–380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e. s.c., i.p., i.v.). Drugs are prepared in methylcellulose, water or other specified vehicle (examples include PEG400, 30% beta-cyclo dextran and propylene glycol). Oxygen consumption and ambulatory activity are measured every 10 minutes for an additional 1–6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption *100. Experiments will typically be done with n=4–6 rats and results reported are mean+/−SEM.

Interpretation:

An increase in oxygen consumption of >10% is considered a positive result. Historically, vehicle-treated rats have no change in oxygen consumption from pre-dose basal.

What is claimed is:

1. A compound of Formula (I)

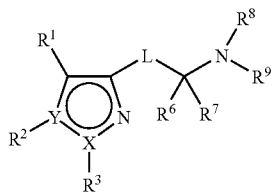

(I)

wherein
- X is carbon and Y is nitrogen or X is nitrogen and Y is carbon;
- $R^1$ is hydrogen, $(C_1–C_6)$alkyl, halogen, or cyano;
- $R^2$ and $R^3$ are each independently $(CH_2)_n$-aryl or $(CH_2)_n$-heteroaryl, where n is 0, 1 or 2, and where said aryl and said heteroaryl moieties are optionally substituted with one or more substituents;
- L is —C(O)— or —C($R^4$)($OR^5$)—, where $R^4$ is hydrogen or $(C_1–C_6)$alkyl and $R^5$ is hydrogen, $(C_1–C_6)$alkyl, or taken together with $R^8$ or $R^9$ to form a morpholine or morpholin-3-one;
- $R^6$ and $R^7$ are each independently hydrogen or $(C_1–C_6)$alkyl, or $R^6$ and $R^7$ taken together form a partially or fully saturated carbocyclic ring; and
- $R^8$ and $R^9$ are each independently hydrogen, $(C_1–C_6)$alkyl, —C(O)$(CH_2)_m R^{10}$, —$SO_2(CH_2)_n R^{10}$, or —$(CH_2)_p R^{10}$, where m and n are 0, 1, or 2, p is 0, 1, 2 or 3, and $R^{10}$ is selected from the group consisting of $(C_1–C_8)$alkyl, a partially or fully saturated cycloalkyl, aryl, heteroaryl, and a partially or fully saturated heterocycle, where said $(C_1–C_8)$alkyl, said cycloalkyl, said aryl, said heteroaryl and said heterocycle are optionally substituted with one or more substituents;
- a pharmaceutically acceptable salt thereof, a prodrug of said compound or said salt, or a solvate or hydrate of said compound, said salt or said prodrug.

2. The compound of claim 1, wherein said compound of Formula (I) is a compound of Formula (IA)

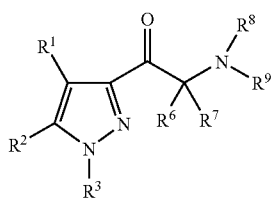

(IA)

wherein
- $R^1$ is hydrogen or $(C_1–C_6)$alkyl;
- $R^2$ and $R^3$ are each independently —$(CH_2)_n$-aryl or —$(CH_2)_n$-heteroaryl, where n is 0, 1 or 2, and where said aryl and said heteroaryl moieties are each optionally substituted with one to three substituents; and
- $R^6$ and $R^7$ are each independently hydrogen or $(C_1–C_6)$alkyl, or $R^6$ and $R^7$ taken together form a partially or fully saturated carbocyclic ring; and a pharmaceutically acceptable salt thereof, a prodrug of said compound or said salt, or a solvate or hydrate of said compound, said salt or said prodrug.

3. The compound of claim 1, wherein said compound of Formula (I) is a compound of Formula (IB)

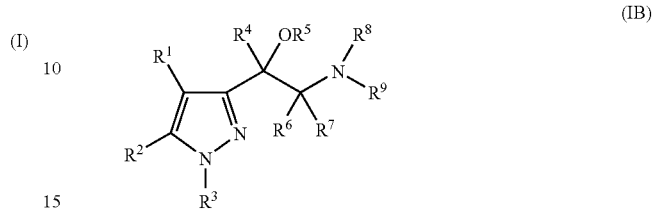

(IB)

wherein
- $R^1$ is hydrogen or $(C_1–C_6)$alkyl;
- $R^2$ and $R^3$ are each independently —$(CH_2)_n$-aryl or —$(CH_2)_n$-heteroaryl, where n is 0, 1 or 2, and where said aryl and said heteroaryl moieties are each optionally substituted with one to three substituents;
- $R^4$ is hydrogen or $(C_1–C_6)$alkyl;
- $R^5$ is hydrogen or $(C_1–C_6)$alkyl;
- $R^6$ and $R^7$ are each independently hydrogen or $(C_1–C_6)$alkyl, or $R^6$ and $R^7$ taken together form a partially or fully saturated carbocyclic ring; and
- $R^8$ and $R^9$ are each independently hydrogen, $(C_1–C_6)$alkyl, —C(O)$(CH_2)_m R^{10}$, —$SO_2(CH_2)_n R^{10}$, or —$(CH_2)_p R^{10}$, where m and n are 0, 1, or 2, p is 0, 1, 2 or 3, and $R^{10}$ is selected from the group consisting of $(C_1–C_8)$alkyl, a partially or fully saturated cycloalkyl, aryl, heteroaryl, and a partially or fully saturated heterocycle, where said $(C_1–C_8)$alkyl, said cycloalkyl, said aryl, said heteroaryl and said heterocycle are optionally substituted with one or more substituents, or a pharmaceutically acceptable salt thereof, a prodrug of said compound or said salt, or a solvate or hydrate of said compound, said salt or said prodrug.

4. The compound of claim 1 wherein said compound of Formula (I) is a compound of Formula (IC)

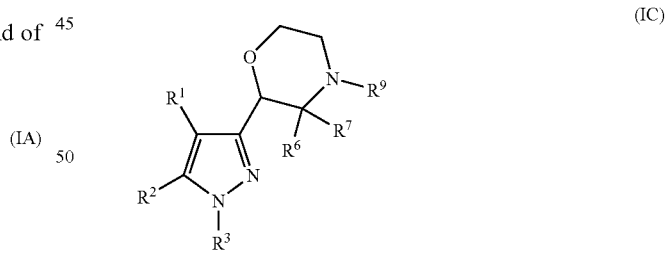

(IC)

wherein
- $R^1$ is hydrogen or $(C_1–C_6)$alkyl;
- $R^2$ and $R^3$ are each independently —$(CH_2)_n$-aryl or —$(CH_2)_n$-heteroaryl, where n is 0, 1 or 2, and where said aryl and said heteroaryl moieties are each optionally substituted with one to three substituents;
- $R^6$ and $R^7$ are each independently hydrogen or $(C_1–C_6)$alkyl, or $R^6$ and $R^7$ taken together form a partially or fully saturated carbocyclic ring; and
- $R^9$ is hydrogen, $(C_1–C_6)$alkyl, —C(O)$(CH_2)_m R^{10}$, —$SO_2(CH_2)_n R^{10}$, or —$(CH_2)_p R^{10}$, where m and n are 0, 1, or 2, p is 0, 1, 2 or 3, and $R^{10}$ is selected from the group consisting of $(C_1-C_8)$alkyl, a partially or fully saturated cycloalkyl, aryl, heteroaryl, and a partially or fully saturated heterocycle, where said $(C_1-C_8)$alkyl, said cycloalkyl, said aryl, said heteroaryl and said heterocycle are optionally substituted with one or more substituents;

a pharmaceutically acceptable salt thereof, a prodrug of said compound or said salt, or a solvate or hydrate of said compound, said salt or said prodrug.

5. The compound of claim 4 selected from the group consisting of
2-[5-(4-chloro-phenyl)-1-(2-chloro-phenyl)-4-methyl-1H-pyrazol-3-yl]-4-cyclohexyl-morpholine;
2-[5-(4-chloro-phenyl)-1-(2-chloro-phenyl)-4-methyl-1H-pyrazol-3-yl]-4-(propane-2-sulfonyl)-morpholine;
2-[5-(4-chloro-phenyl)-1-(2-chloro-phenyl)-4-methyl-1H-pyrazol-3-yl]-4-(toluene-4-sulfonyl)-morpholine;
1-{2-[1-(2-chloro-phenyl)-5-(4-chloro-phenyl)-4-methyl-1H-pyrazol-3-yl]-morpholin-4-yl}-2-methyl-propan-1-one;
2-[1-(2-chloro-phenyl)-5-(4-chloro-phenyl)-4-methyl-1H-pyrazol-3-yl]-4-(4-trifluoromethyl-benzyl)-morpholine; and a pharmaceutically acceptable salt thereof or a solvate or hydrate of said compound or said salt.

6. The compound of claim 1, wherein said compound of Formula (I) is a compound of Formula (ID)

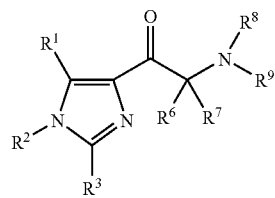

(ID)

wherein
$R^1$ is hydrogen or $(C_1-C_6)$alkyl;
$R^2$ and $R^3$ are each independently —$(CH_2)_n$-aryl or —$(CH_2)_n$-heteroaryl, where n is 0, 1 or 2, and where said aryl and said heteroaryl moieties are each optionally substituted with one to three substituents;
$R^6$ and $R^7$ are each independently hydrogen or $(C_1-C_6)$ alkyl, or $R^6$ and $R^7$ taken together form a partially or fully saturated carbocyclic ring; and
$R^8$ and $R^9$ taken together form a partially or fully saturated, 5- to 7-membered heterocyclic ring containing 1 to 3 heteroatoms and optionally substituted with one or more substituents;

a pharmaceutically acceptable salt thereof, a prodrug of said compound or said salt, or a solvate or hydrate of said compound, said salt or said prodrug.

7. The compound of claim 1, 2, 3, 4, or 6 wherein $R^2$ is p-chlorophenyl or p-fluorophenyl, and $R^3$ is 2,4-dichlorophenyl, 2-chlorophenyl or 2-flurorophenyl.

8. A pharmaceutical composition comprising
(a) a compound of claim 1, a pharmaceutically acceptable salt thereof, or a solvate or hydrate of said compound or said salt; and
(b) a pharmaceutically acceptable excipient, diluent, or carrier.

9. A method for treating a disease, condition or disorder modulated by a cannabinoid receptor antagonist in animals comprising the step of administering to an animal in need of such treatment a therapeutically effective amount of a compound of claim 1, a pharmaceutically acceptable salt thereof, or a solvate or hydrate of said compound or said salt wherein said disease, condition or disorder modulated by a cannabinoid receptor antagonist is selected from the group consisting of weight loss, obesity, bulimia, depression, bipolar disorders, psychoses, schizophrenia, behaviors, alcoholism, tobacco abuse, memory loss, Alzheimer's disease, dementia of aging, seizure disorders, epilepsy, attention deficit disorder, Parkinson's disease, and type II diabetes.

10. The method of claim 9 wherein said disease is obesity, bulimia, attention deficit disorder, alcoholism, or tobacco abuse.

11. The compound selected from the group consisting of
2-(Benzyl-isopropyl-amino)-1-[1-(2-chlorophenyl)-5-(4-chlorophenyl)-4-methyl-1H-pyrazol-3-yl]-ethanone hydrochloride salt;
2-(Benzyl-isopropyl-amino)-1-[1-(2-chlorophenyl)-5-(4-chlorophenyl)-4-methyl-1H-pyrazol-3-yl]-ethanol;
2-(Benzyl-isopropyl-amino)-1-[1-(2-chlorophenyl)-5-(4-chlorophenyl)-4-methyl-1H-pyrazol-3-yl]-ethanol hydrochloride;
2-[Benzyl-(2-hydroxy-ethyl)-amino]-1-[5-(4-chlorophenyl)-1-(2-chlorophenyl)-4-methyl-1H-pyrazol-3-yl]-ethanol;
1-Benzylamino-1-[5-(4-chlorophenyl)-1-(2-chlorophenyl)-4-methyl-1H-pyrazol-3-yl]-ethanol hydrochloride;
benzyl-{2-[1-(2-chlorophenyl)-5-(4-chlorophenyl)-4-methyl-1H-pyrazol-3-yl]-2-methoxy-ethyl}-isopropyl-amine; and
1-(Benzyl-isopropyl-amino)-2-[1-(2-chlorophenyl)-5-(4-chlorophenyl)-4-methyl-1H-pyrazol-3-yl]-propan-2-ol;

or a pharmaceutically acceptable salt thereof or a solvate or hydrate of said compound or said salt.

* * * * *